(12) United States Patent
Tsantrizos et al.

(10) Patent No.: US 7,582,766 B2
(45) Date of Patent: Sep. 1, 2009

(54) INHIBITORS OF PAPILLOMA VIRUS

(75) Inventors: Youla S. Tsantrizos, Montreal (CA); Anne-Marie Faucher, St-Placide (CA); Jean Rancourt, Laval (CA); Peter White, Montreal (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 584 days.

(21) Appl. No.: 10/862,264

(22) Filed: Jun. 7, 2004

(65) Prior Publication Data

US 2005/0014791 A1 Jan. 20, 2005

Related U.S. Application Data

(60) Provisional application No. 60/477,064, filed on Jun. 9, 2003.

(51) Int. Cl.
*A61K 31/445* (2006.01)
*C07D 211/08* (2006.01)

(52) U.S. Cl. ...................... 546/192; 514/317
(58) Field of Classification Search ............... 546/192; 514/317
See application file for complete search history.

(56) References Cited

U.S. PATENT DOCUMENTS

| 4,735,959 A | * | 4/1988 | Grell et al. ............... 514/357 |
| 5,312,924 A | | 5/1994 | Gerhart et al. | |

FOREIGN PATENT DOCUMENTS

| DE | 3225155 A1 | * | 12/1984 |
| DE | 3347565 | * | 11/1985 |
| DE | 37 23 232 | | 1/1989 |
| FR | 2 763 590 | | 11/1998 |
| GB | 2 090 834 | | 7/1982 |
| GB | 2 124 220 | | 2/1984 |
| WO | WO 97/19062 | | 5/1997 |
| WO | WO 99/55663 | | 11/1999 |

OTHER PUBLICATIONS

Wolfgang Grell et al. Repaglinide and related hypoglycemic Benzoic acid Derivative., 1998, 41, pp. 5219-5246.*
Database Caplus Chemical Abstracts Service, Columbus, Ohio, US; Lebegue, N., et al: "Synthesis of ortho-methoxyphenylsulfonylsemicarbazides" retrieved from STN Database accession No. 2004:202542, XP002305085 the compound with the RN:700359-72-4!
N. Lebegue, et al. "Synthesis of ortho-Methoxyphenylsulfonylsemicarbazides", Synthetic Communications, vol. 34, No. 6, pp. 1041-1048, 2004.

* cited by examiner

*Primary Examiner*—Rita J Desai
(74) *Attorney, Agent, or Firm*—Michael P. Morris; Mary-Ellen M. Devlin; David A. Dow

(57) ABSTRACT

The use of a compound of formula (II):

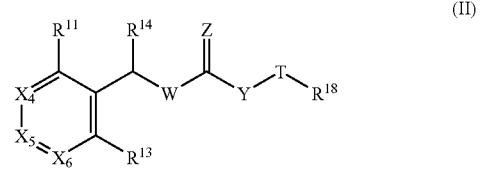

or its enantiomers or diastereoisomers thereof, or salts or pharmaceutically-acceptable esters thereof, in the treatment or prevention of a papilloma virus infection, particularly human papilloma virus in a mammal, wherein $R^{11}$; $X_4$; $X_5$; $X_6$; $R^{13}$; $R^{14}$; W; Z; Y; T; and $R^{18}$ are defined herein.

The present invention also provides novel compounds, pharmaceutical compositions and methods for using these compounds and compositions in the treatment or prevention of papilloma virus infection. More particularly, the present invention provides compounds, compositions and methods for inhibiting papilloma virus DNA replication by interfering with the E1-E2 protein-protein interaction essential for viral DNA replication.

15 Claims, No Drawings

INHIBITORS OF PAPILLOMA VIRUS

FIELD OF THE INVENTION

The present invention relates to compounds, compositions and methods for the treatment or prevention of papilloma virus (PV) infection, particularly human papilloma virus (HPV). In particular, the present invention provides novel compounds, pharmaceutical compositions containing such compounds and methods for using these compounds in the treatment or prevention of papilloma virus infection. More particularly, the present invention provides compounds, compositions and methods for inhibiting papilloma virus DNA replication by interfering with the E1-E2 protein-protein interaction during initiation of viral DNA replication.

BACKGROUND OF THE INVENTION

Papillomaviruses are non-enveloped DNA viruses that induce hyperproliferative lesions of the epithelia. The papillomaviruses are widespread in nature and have been identified in higher vertebrates. Viruses have been characterized, amongst others, from humans, cattle, rabbits, horses, and dogs. The first papillomavirus was described in 1933 as cottontail rabbit papillomavirus (CRPV). Since then, the cottontail rabbit as well as bovine papillomavirus type 1 (BPV-1) have served as experimental prototypes for studies on papillomaviruses. Most animal papillomaviruses are associated with purely epithelial proliferative lesions, and most lesions in animals are cutaneous. In the human, there are more than 75 types of papillomavirus that have been identified and they have been catalogued by site of infection: cutaneous epithelium and mucosal epithelium (oral and genital mucosa). The cutaneous-related diseases include flat warts, plantar warts, etc. The mucosal-related diseases include laryngeal papillomas and anogenital diseases such as cervical carcinomas.

There are more than 25 HPV types that are implicated in anogenital diseases, these are grouped into "low risk" and "high risk" types. The low risk types include HPV type 6 and type 11, and induce mostly benign lesions such as condyloma acuminata (genital warts) and low grade squamous intraepithelial lesions (SIL). In the United States, 1% of the sexually active population has genital warts of which 90% is attributed to HPV-6 and HPV-11.

The high risk types are associated with high grade SIL, cervical and anal cancers and include most frequently HPV types 16, 18, 31, 33, 35, 45, 52, and 58. The progression from low-grade SIL to high-grade SIL is much more frequent for lesions that contain high risk HPV-16 and 18 as compared to those that contain low risk HPV types. In addition, only four HPV types are detected frequently in cervical cancer (types 16, 18, 31 and 45). About 500,000 new cases of invasive cancer of the cervix are diagnosed annually worldwide.

Treatments for genital warts include physical removal such as cryotherapy, $CO_2$ laser, electrosurgery, or surgical excision. Cytotoxic agents may also be used such as trichloroacetic acid (TCA), podophyllin or podofilox. Immunomodulatory therapy is also available such as interferon or imiquimod. These treatments are not completely effective in eliminating all viral particles and there is either a high cost incurred or uncomfortable side effects related thereto. In fact, there are currently no commercially available effective antiviral treatments for HPV infection since recurrent warts are common with all current therapies.

The ineffectiveness of the current methods to treat HPV infections has demonstrated the need to identify new means to control or eliminate such infections. In recent years, efforts have been directed towards finding antiviral compounds, and especially compounds capable of interfering with viral replication at the onset of infection.

The life cycle of PV is closely coupled to keratinocyte differentiation. Infection is believed to occur at a site of tissue disruption in the basal epithelium. Unlike normal cells, the cellular DNA replication machinery is maintained as the cell undergoes vertical differentiation. As the infected cells undergo progressive differentiation the viral genome copy number and viral gene expression in turn increase, with the eventual late gene expression and virion assembly in terminally differentiated keratinocytes and the release of viral particles.

The coding strands for each of the papillomaviruses contain approximately ten designated translational open reading frames (ORFs) that have been classified as either early ORFs or late ORFs based on their location in the genome. E1 to E8 are expressed early in the viral replication cycle, and two late genes (L1 and L2) encode the major and minor capsid proteins respectively. The E1 and E2 gene products function in viral DNA replication, whereas E5, E6 and E7 are expressed in connection with host cell proliferation. The L1 and L2 gene products are involved in virion structure. The function of the E3 and E8 gene products is uncertain at present.

Studies of HPV have shown that proteins E1 and E2 are the only two viral proteins that are necessary for viral DNA replication in vitro and in vivo, in addition to the host DNA replication machinery. This requirement is similar to that of bovine papillomavirus type 1 (BPV-1). Indeed, there is a high degree of similarity between E1 and E2 proteins and the ori-sequences of all papillomaviruses (PV) regardless of the viral species and type. Evidence emanating from studies of BPV-1 have shown that E1 possesses ATPase and helicase activities that are required in viral DNA replication.

The E2 protein is a transcriptional activator that binds to E1 protein and forms a complex that binds specifically to the ori sequence (Mohr et al., 1990, Science 250:1694-1699), an interaction that is essential for viral DNA replication. It is believed that E2 enhances binding of E1 to the BPV origin of replication (Seo et al., 1993b, Proc. Natl. Acad. Sci., 90:2865-2869). In HPV, Liu et al. suggested that E2 stabilizes E1 binding to the ori (1995, J. Biol. Chem., 270(45):27283-27291).

To thwart this disease, a chemical entity that would interfere with viral DNA replication is therefore desirable, and the development of new and specific anti-PV, particularly anti-HPV, treatments remains a high priority.

WO 02/50082 published on Jun. 27, 2002 discloses novel indanedione derivatives, pharmaceutical compositions containing such derivatives and methods for using these compounds in the treatment of papilloma virus infection.

WO 01/07027 published on Feb. 1, 2001 to Vertex Pharmaceuticals Incorporated discloses pyrimidine-based inhibitors and analogs thereof for use in inhibiting viral helicases, including viral helicases of flaviviruses, poxviruses and papova viruses.

WO 99/55663 published on Nov. 4, 1999 to Vertex Pharmaceuticals Incorporated discloses substituted aryl compounds and derivatives thereof as inhibitors of inosine-5'-monophosphate dehydrogenase enzyme activity which are useful for mediating IMDH mediated processes, including human papilloma virus replication.

None of the prior art teaches compounds of the present invention as inhibitors of papilloma viral DNA replication.

Structures related to the compounds of the present invention are described in the following patent documents: WO 97/45400, WO 98/47879, and WO 00/24707 of Neurosearch;

WO 00/71508; WO 00/71507; WO 00/71509 and WO 00/71493 of Cor Therapeutics; WO 97/49286, WO 00/76501, and WO 00/69435 of SmithKline Beecham; EP 0 974 576 of Mitsui Chemicals; WO 97/24328 and WO 01/02350 of Bayer AG; WO 94/06280 of the University of California; WO 95/11880 of Merck Sharpe & Dohme; and FR 2 763 590 of Synthelabo; U.S. Pat. No. 5,312,924, U.S. Pat. No. 5,216,167; GB 2 124 220 and GB 2 090 834 of Dr. Karl Thomae; U.S. Pat. No. 4,943,315, WO 01/90079 and GB 2 289 893 of BASF AG; JP 09 087237 of Kyowa Hakko Kogya Co.; CA 2,191,757 of Hoechst Schering AgrEvo; EP 0 656 349 and EP 0 588 655 of Ono Pharmaceutical; and EP 0 528 586 of Merck & Co. None of these references teach that such related compounds can be useful in the treatment or prevention of papilloma virus infection.

The present invention therefore provides novel compounds, compositions and methods that inhibit papilloma viral replication. More particularly, the compounds and composition of the present invention interfere with the E1-E2 protein-protein interaction during the viral replication cycle.

SUMMARY OF THE INVENTION

In a first aspect, the invention provides a compound of formula (I) or its enantiomers or diastereoisomers thereof:

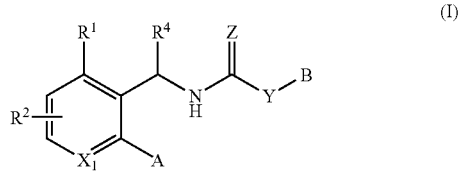

wherein $R^1$ is H, $(C_{1-6})$alkyl, halo, $(C_{1-6})$haloalkyl; $(C_{1-6})$alkoxy, $(C_{1-6})$alkylthio, amino, $(C_{1-6})$alkylamino, di($(C_{1-6})$alkyl)amino, $(C_{3-7})$cycloalkyl, phenyl, or 5- or 6-membered heterocycle;

$X_1$ is $CR^2$ or N;

one or both free positions on the phenyl ring may be substituted with $R^2$ and each $R^2$ is independently selected from: H, $(C_{1-6})$alkyl, halo, $(C_{1-6})$haloalkyl, $(C_{1-6})$alkoxy, $(C_{1-6})$alkylthio, amino, $(C_{1-6})$alkylamino and di($(C_{1-6})$alkyl)amino;

A is $(C_{3-7})$cycloalkyl, aryl or heterocycle, each of which being optionally substituted with one or more substituents independently selected from:
$(C_{1-6})$alkyl, halo, $(C_{1-6})$haloalkyl, $(C_{1-6})$alkoxy, $(C_{1-6})$alkylthio, amino, $(C_{1-6})$alkylamino, or di($(C_{1-6})$alkyl)amino, aryl, O-aryl, S-aryl, NH-aryl, $(C_{1-6})$alkyl-aryl, heteroaryl, O-heteroaryl, S-heteroaryl, NH-heteroaryl and $(C_{1-6})$alkyl-heteroaryl;

or A is $NHR^3$ or $N(R^3)_2$ wherein
    each $R^3$ is independently selected from H, $(C_{1-6})$alkyl, $(C_{3-7})$cycloalkyl, aryl and heteroaryl;

$R^4$ is $(C_{1-6})$alkyl, $(C_{3-7})$cycloalkyl, aryl, heterocycle, $(C_{1-6})$alkyl-aryl or $(C_{1-6})$alkyl-heterocycle, each of which being optionally substituted with one or more substituents independently selected from:
    $(C_{1-6})$alkyl, halo, $(C_{1-6})$haloalkyl, $(C_{1-6})$alkylthio, amino, $(C_{1-6})$alkylamino, di($(C_{1-6})$alkyl)amino, aryl, heteroaryl, $(C_{1-6})$alkyl-aryl, $(C_{1-6})$alkyl-heteroaryl, and $(C_{1-6})$alkoxy, wherein said $(C_{1-6})$alkoxy is optionally substituted with aryl or heteroaryl;

or $R^4$ is phenyl fused with a saturated or unsaturated 4- to 6-membered ring optionally containing one to three heteroatoms independently selected from N, O, and S;

Z is O or S;

Y is $CH_2$, NH or O;

B is selected from:

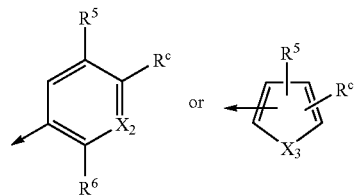

wherein $R^5$ is H, $(C_{1-6})$alkyl, $(C_{3-7})$cycloalkyl, halo, $(C_{1-6})$haloalkyl, $(C_{1-6})$alkoxy, $(C_{1-6})$alkylthio, amino, $(C_{1-6})$alkylamino, di($(C_{1-6})$alkyl)amino, hydroxyl or sulfhydryl;

$X_2$ is $CR^7$ or N;

$R^6$ and $R^7$ are independently H, $(C_{1-6})$alkyl, halo, $(C_{1-6})$haloalkyl, $(C_{1-6})$alkoxy, $(C_{1-6})$alkylthio, amino, $(C_{1-6})$alkylamino, di($(C_{1-6})$alkyl)amino, hydroxyl or sulfhydryl;

or, when $X_2$ is $CR^7$, $R^6$ and $R^7$ are optionally bonded together to form a saturated or unsaturated 5- or 6-membered ring optionally containing one or two heteroatoms independently selected from S, O and N;

$X_3$ is O, S or $NR^8$, wherein $R^8$ is H or $(C_{1-6})$alkyl; and $R^c$ is COOH, $CONHR^9$, $SO_2NHR^9$, $CONHSO_2R^9$, $CONHSO_2NHR^9$, triazolyl or tetrazolyl,
    wherein $R^9$ is H, $(C_{1-6})$alkyl, $(C_{3-6})$cycloalkyl or phenyl;

provided that $R^5$ and $R^6$ cannot both together be H and when $R^5$ or $R^6$ is H, then $R^1$ is not H, and provided that when Y is NH, $R^6$ cannot be hydroxyl or sulfhydryl;

or a pharmaceutically-acceptable salt or ester thereof.

Included within the scope of this invention are compounds of the formula (I) as described hereinbefore, to which at least one of a "detectable label", an "affinity tag" or a "photoreactive group" is linked.

In a second aspect, the invention provides the use of a compound of formula (I) above in the manufacture of a medicament for the treatment or prevention of papilloma virus infection in a mammal.

In a third aspect, the invention provides the use of a compound of formula (II) or its enantiomers or diastereoisomers thereof, in the manufacture of a medicament for the treatment or prevention of a papilloma virus infection in a mammal:

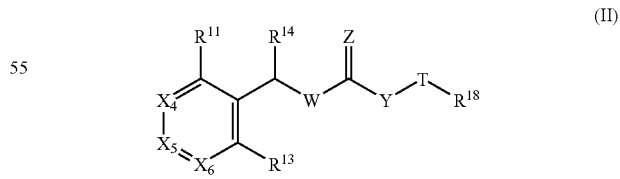

wherein $R^{11}$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, di($(C_{1-6})$alkyl)amino, $(C_{3-7})$cycloalkyl, phenyl, or 5- or 6-membered heterocycle;

$X_4$, $X_5$ and $X_6$ are independently chosen from $CR^{12}$ and N, wherein each $R^{12}$ is independently selected from: H, $(C_{1-6})$alkyl, $(C_{1-6})$alkoxy, halo, $(C_{1-6})$alkylthio, $(C_{1-6})$haloalkyl, amino, $(C_{1-6})$alkylamino and $di((C_{1-6})$alkyl)amino;

$R^{13}$ is $(C_{1-6})$alkyl, $(C_{3-7})$cycloalkyl, aryl, or heterocycle, said $(C_{1-6})$alkyl, $(C_{3-7})$cycloalkyl, aryl and heterocycle being optionally substituted with $R^{15}$ wherein $R^{15}$ is H, $(C_{1-6})$alkyl, $(C_{3-7})$cycloalkyl, halo, $(C_{1-6})$haloalkyl, $(C_{1-6})$alkoxy, $(C_{1-6})$alkylthio, amino, $(C_{1-6})$alkylamino, or $di((C_{1-6})$alkyl)amino, aryl, O-aryl, S-aryl, NH-aryl, $(C_{1-6})$alkyl-aryl, heteroaryl, O-heteroaryl, S-heteroaryl, NH-heteroaryl or $(C_{1-6})$alkyl-heteroaryl;

or $R^{13}$ is $OR^{16}$, $SR^{16}$, $NHR^{16}$ or $N(R^{16})_2$ wherein
$R^{16}$ is independently selected in each instance from: H, $(C_{1-6})$alkyl, $(C_{3-7})$cycloalkyl, aryl and heteroaryl; and $R^{14}$ is H, $(C_{1-6})$alkyl, $(C_{3-7})$cycloalkyl, aryl, heterocycle, $(C_{1-6})$alkyl-aryl or $(C_{1-6})$alkyl-heterocycle, wherein said $(C_{1-6})$alkyl, $(C_{3-7})$cycloalkyl, aryl, heterocycle, $(C_{1-6})$alkyl-aryl or $(C_{1-6})$alkyl-heterocycle are optionally substituted with one or more substituents independently selected from:

$(C_{1-6})$alkyl, halo, $(C_{1-6})$haloalkyl, $(C_{1-6})$alkylthio, amino, $(C_{1-6})$alkylamino, $di((C_{1-6})$alkyl)amino, aryl, heteroaryl, $(C_{1-6})$alkyl-aryl, $(C_{1-6})$alkyl-heteroaryl, and $(C_{1-6})$alkoxy, wherein said $(C_{1-6})$alkoxy is optionally substituted with aryl or heteroaryl;

or $R^{14}$ is phenyl fused with a saturated or unsaturated 4- to 6-membered ring optionally containing one to four heteroatoms independently selected from N, O, and S;

or $R^{14}$ is $CH_2COOR^{17}$ or $CH_2CONHR^{17}$, wherein
$R^{17}$ is $(C_{1-6})$alkyl, $(C_{3-7})$cycloalkyl, aryl or heterocycle, said $(C_{1-6})$alkyl, $(C_{3-7})$cycloalkyl, aryl and heterocycle being optionally further substituted with:
aryl or heteroaryl, both being optionally substituted with one to four $R^{11}$;

W is NH or $CH_2$;
Z is O or S;
Y is $CH_2$, NH or O;
T is aryl, or heteroaryl, said aryl and heteroaryl being optionally substituted with:
one to three $R^{11}$, hydroxyl or sulfhydryl; and
$R^{18}$ is COOH, $COOR^{19}$, $CONHR^{19}$, $SO_2NHR^{19}$, $CONHSO_2R^{19}$, $CONHSO_2NHR^{19}$, triazolyl or tetrazolyl; wherein
$R^{19}$ is H, $(C_{1-6})$alkyl, $(C_{3-6})$cycloalkyl or phenyl;

or a pharmaceutically acceptable salt or ester thereof.

In a preferred embodiment, the papilloma virus is a human papilloma virus. In a more preferred embodiment, the human papilloma virus comprises a low risk type human papilloma virus, preferably type 6 or type 11 human papilloma virus.

In a fourth aspect, the invention provides a pharmaceutical composition comprising a therapeutically effective and acceptable amount of a compound of formula (I) in association with at least one pharmaceutically-acceptable carrier.

In a fifth aspect, the invention provides a pharmaceutical composition for use in the treatment or prevention of papilloma virus infection, wherein the composition comprises a therapeutically effective and acceptable amount of a compound of formula (I) or formula (II), in association with at least one pharmaceutically-acceptable carrier.

In a sixth aspect, the invention provides an anti-papilloma virus pharmaceutical composition comprising an anti-papilloma virus virally-effective amount of a compound of formula (I), or a compound of formula (II), in association with at least one pharmaceutically-acceptable carrier.

In a seventh aspect, the invention provides a use of a compound of formula (I) or a compound of formula (II), to inhibit the replication of a papilloma virus.

In an eighth aspect, the invention provides a use of a compound of formula (I) or a compound of formula (II), in the treatment or prevention of a papilloma virus infection in a mammal.

In a ninth aspect, the invention provides a use of a compound of formula (I) or formula (II) for binding to the E2 transcriptional activation domain of the human papilloma virus E2 protein to inhibit binding of the E2 protein to the human papilloma virus E1 protein, to inhibit viral DNA replication in a mammal infected with a human papilloma virus.

In a tenth aspect, the invention provides a use of a compound of formula (I) or formula (II) for inhibiting the human papilloma virus E1-E2 protein-protein interaction to inhibit papilloma virus viral DNA replication in a mammal infected with the virus.

In an eleventh aspect, the invention provides a method of treating or preventing a papilloma virus infection in a mammal comprising administering to the mammal an anti-papilloma virus virally-effective and acceptable amount of a compound of formula (I) or formula (II), or a composition containing such a compound.

In a twelfth aspect, the invention provides a method of inhibiting replication of a papilloma virus comprising exposing the virus to an anti-papilloma virus virally-effective and acceptable amount of a compound of formula (I) or a compound of formula (II), thereby inhibiting the human papilloma virus E1-E2 protein-protein interaction.

In a thirteenth aspect, the invention provides a method of inhibiting replication of a papilloma virus comprising exposing virally-infected cells to a anti-papilloma virus virally-effective and acceptable amount of at least one of a compound of formula (I) and a compound of formula (II).

In a fourteenth aspect, the invention provides a packaged pharmaceutical comprising a pharmaceutical composition containing a compound of formula (I) or of formula (II) and directions identifying an administration regimen.

In a fifteenth aspect, the invention provides a packaged pharmaceutical for use for the treatment or prevention of papilloma virus infection in a mammal, wherein the packaged pharmaceutical comprises a pharmaceutical composition containing a compound of formula (I) or formula (II) and directions identifying an administration regimen.

In a sixteenth aspect, the invention provides an article of manufacture comprising packaging material contained within which is a composition effective to inhibit a papilloma virus and the packaging material comprises a label which indicates that the composition can be used to treat or prevent infection by a papilloma virus, wherein said composition includes a compound of formula (I) or a compound of formula (II).

DETAILED DESCRIPTION OF THE PREFERRED EMBODIMENTS

Definitions

Unless defined otherwise, the scientific and technological terms and nomenclature used herein have the same meaning as commonly understood by a person skilled in the art to which this invention pertains but should not be interpreted as limiting the scope of the present invention.

The term "eutomer" as used herein means the enantiomer, from a pair of enantiomers, that is more active i.e. has the highest biological potency.

The term "distomer" as used herein means the enantiomer, from a pair of enantiomers, that is less active or has no potency.

The term "halo" as used herein means a halogen radical selected from bromo, chloro, fluoro or iodo.

The term "hydroxyl" as used herein means an —OH radical.

The term "sulfhydryl" as used herein means a —SH radical.

The term "$(C_{1-n})$alkyl" as used herein, either alone or in combination with another radical, means straight or branched-chain alkyl radicals containing from one to n carbon atoms and includes, but is not limited to, methyl, ethyl, propyl, butyl, hexyl, 1-methylethyl, 1-methylpropyl, 2-methylpropyl and 1,1-dimethylethyl.

The term "$(C_{3-n})$cycloalkyl" as used herein, either alone or in combination with another radical, means saturated cyclic hydrocarbon radicals containing from three to n carbon atoms. The term "$(C_{3-7})$cycloalkyl" includes cyclopropyl, cyclobutyl, cyclopentyl, cyclohexyl and cycloheptyl.

The terms "$(C_{1-n})$alkoxy" or "O—$(C_{1-n})$alkyl" as used herein interchangeably, mean a straight chain alkyl containing from one to n carbon atoms linked through an oxygen atom or a branched chain alkyl radical containing three to n carbon atoms linked through an oxygen atom. Examples of $(C_{1-6})$alkoxy include, but are not limited to, methoxy ($CH_3O$—), ethoxy ($CH_3CH_2O$—), propoxy ($CH_3CH_2CH_2O$—), 1-methylethoxy (($CH_3)_2CHO$—), butoxy ($CH_3CH_2CH_2CH_2O$—) and 1,1-dimethyl ethoxy (($CH_3)_3CO$—). The latter radical is known commonly as tert-butoxy. When a $(C_{1-n})$alkoxy group is substituted with one or more substituents, for example, aryl or heteroaryl substituents, said substituents are attached to the alkyl portion of the alkoxy group.

The term "$(C_{1-n})$haloalkyl" as used herein means an alkyl radical containing one to n carbon atoms wherein one or more hydrogen atoms are replaced by a halogen atom (e.g. trifluoromethyl).

The terms "$(C_{1-n})$alkylthio" or "S—$(C_{1-n})$alkyl" as used herein interchangeably, mean a straight chain alkyl containing one to n carbon atoms linked through a sulfur atom, or a branched chain alkyl radical containing three to n carbon atoms linked through a sulfur atom. Examples of $(C_{1-n})$alkylthio include, but are not limited to, methylthio ($CH_3S$—), ethylthio ($CH_3CH_2S$—), propylthio ($CH_3CH_2CH_2S$—), 1-methylethylthio (($CH_3)_2CHS$—), butylthio ($CH_3CH_2CH_2CH_2S$—) and 1,1-dimethylethylthio (($CH_3)_3CS$—).

The term "amino" as used herein means an amino radical of formula —$NH_2$. The term "$(C_{1-n})$alkylamino" as used herein means an alkylamino radical containing one to n carbon atoms and includes, but is not limited to, methylamino, propylamino, (1-methylethyl)amino and (2-methylbutyl)amino. The term "di(($C_{1-n})$alkyl)amino" means an amino radical having two identical or different $(C_{1-n})$alkyl substituents and includes, but is not limited to, dimethylamino, diethylamino, ethylmethylamino and the like.

The term "aryl" as used herein, either alone or in combination with another radical, means a phenyl ring which is optionally fused to a second carbocyclic ring, wherein said carbocyclic ring contains 5 to 7 carbon atoms and may be saturated, unsaturated or aromatic. For example, aryl includes, but is not limited to, phenyl, naphthyl,

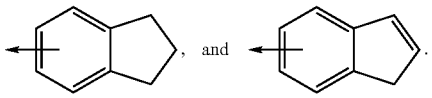

The terms "aryloxy" or "O-aryl" as used herein interchangeably, mean an aryl as defined above linked though an oxygen atom. Examples of aryloxy include, but are not limited to, phenoxy.

The term "$(C_{1-n})$alkyl-aryl" as used herein, either alone or in combination with another radical, means an aryl as defined above linked through an alkyl group, wherein alkyl is as defined above containing from 1 to n carbon atoms. ($C_{1-6}$) alkyl-aryl includes, but is not limited to, benzyl and phenyl-butyl.

The term "Het" or "heterocycle" as used herein means a monovalent radical derived by removal of a hydrogen from a four- to seven-membered, saturated or unsaturated (including aromatic) ring system containing from one to three heteroatoms independently selected from nitrogen, oxygen and sulfur. Optionally, the heterocycle may bear one or two substituents; for example, N-oxide, $(C_{1-6})$alkyl, $(C_{1-3})$alkyl-phenyl, $(C_{1-6})$alkoxy, halo, amino or $(C_{1-6})$alkylamino. Again optionally, the four- to seven-membered heterocycle can be fused to a second ring system which may be saturated or unsaturated (including aromatic) and which may be carbocyclic or may contain from one to three heteroatoms independently selected from nitrogen, oxygen and sulfur. Examples of such a second ring system include, but are not limited to, a cycloalkyl, an aryl (e.g. phenyl) or another heterocycle.

Examples of suitable heterocycles and optionally substituted heterocycles include, but are not limited to, morpholine, thiadiazole, quinoline, benzodioxole, benzothiazole, pyrrolidine, tetrahydrofuran, thiazolidine, pyrrole, indole, benzimidazole, 1H-imidazole, 1-methyl-1H-imidazole, pyrazole, furan, thiophene, oxazole, isoxazole, thiazole, 2-methylthiazole, 2-aminothiazole, 2-(methylamino)thiazole, piperidine, 1-methylpiperidine, 1-methylpiperazine, 1,4-dioxane, pyridine, pyridine N-oxide, pyrimidine, 2,4-dihydroxypyrimidine, 2,4-dimethylpyrimidine, 2,6-dimethylpyridine, 1-methyl-1H-tetrazole, 2-methyl-2H-tetrazole, benzoxazole and thiazolo[4,5-b]-pyridine.

The term "$(C_{1-n})$alkyl-heterocycle" as used herein means a heterocycle as defined above linked through a $(C_{1-n})$alkyl chain, also as defined above.

The term "heteroaryl" as used herein means a monovalent radical derived by removal of a hydrogen from a five- or six-membered, aromatic ring system containing from one to three heteroatoms independently selected from nitrogen, oxygen and sulfur. Optionally, the heteroaryl may bear one or two substituents; for example, N-oxide, $(C_{1-6})$alkyl, $(C_{1-3})$ alkyl-phenyl, $(C_{1-6})$alkoxy, halo, amino or $(C_{1-6})$alkylamino. Again optionally, the five- or six-membered heteroaryl can be fused to a second aromatic ring system which may be carbocyclic or may contain from one to three heteroatoms independently selected from nitrogen, oxygen and sulfur. Examples of such a second ring system include, but are not limited to, aryl (e.g. phenyl) or another heteroaryl. Specifically, heteroaryl includes but is not limited to: indole, benzimidazole, imidazole, furan, thiophene, pyrrole, oxazole, pyridine and pyrimidine.

The term "$(C_{1-n})$alkyl-heteroaryl" as used herein means a heteroaryl as defined above, linked through a $(C_{1-n})$alkyl chain, also as defined above.

As used herein, the designation whereby a bond is drawn as emanating from the center of a ring, such as, for example,

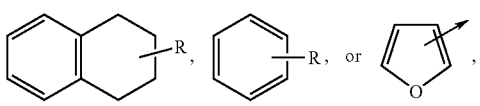

means that the bond may be attached to any free position on the ring that would otherwise be substituted by a hydrogen atom, unless specified otherwise. Such bonds may be linked to substituents of the ring or may indicate the linkage of the ring as a substituent on another structure.

As used herein, the term "detectable label" means any group that may be linked to a compound of the present invention such that when the compound is associated with the target, for example, the transcriptional activation domain of a papillomavirus E2 protein, such label allows recognition either directly or indirectly of the compound such that it can be detected, measured and quantified. Examples of such "labels" are intended to include, but are not limited to, fluorescent labels, chemiluminescent labels, colorimetric labels, enzymatic markers, radioactive isotopes and affinity tags such as biotin. Such labels are attached to the compound or to the protein by well known methods.

As used herein, the term "affinity tag" means a ligand (that may be linked to a compound of the present invention) whose strong affinity for a receptor can be used to extract from a solution the entity to which the ligand is attached. Examples of such ligands include, but are not limited to, biotin or a derivative thereof, a histidine polypeptide, a polyarginine, an amylose sugar moiety or a defined epitope recognizable by a specific antibody. Such affinity tags are attached to the compound by well-known methods.

As used herein, the term "photoreactive group" means a group that is transformed, upon activation by light, from an inert group to a reactive species, such as a free radical. Such a group may be used as, for example, a photoaffinity label. Examples of such groups include, but are not limited to, benzophenones, azides, and the like.

The term "pharmaceutically acceptable carrier" as used herein means a non-toxic, generally inert vehicle for the active ingredient which does not adversely affect the ingredient.

The term "effective amount" means a predetermined antiviral amount of the antiviral agent, i.e. an amount of the agent sufficient to be effective against the virus in vivo.

As used herein, the term "treatment" means the administration of a compound or composition according to the present invention to alleviate or eliminate symptoms of papillomavirus infection and/or to reduce viral load in a patient.

As used herein, the term "prevention" means the administration of a compound or composition according to the present invention post-exposure of the individual to the virus but before the appearance of symptoms of the disease, to prevent the appearance of symptoms of the disease.

The compounds of the present invention can be obtained in the form of therapeutically acceptable salts. The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci. (1977), 66, 1-19).

The term "pharmaceutically acceptable ester" as used herein, either alone or in combination with another radical, means esters of a compound in which the carboxyl function is replaced by an alkoxycarbonyl function:

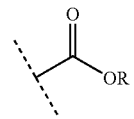

in which the R moiety of the ester is selected from alkyl (e.g. methyl, ethyl, n-propyl, tert-butyl, n-butyl); alkoxyalkyl (e.g. methoxymethyl); acyloxyalkyl (e.g. acetoxymethyl); $(C_{1-6})$ alkyl-aryl (e.g. benzyl); aryloxyalkyl (e.g. phenoxymethyl); aryl (e.g. phenyl), optionally substituted with halogen, $(C_{1-4})$ alkyl or $(C_{1-4})$alkoxy. Other suitable prodrug esters can be found in Design of prodrugs, Bundgaard, H. Ed. Elsevier (1985). Such pharmaceutically acceptable esters are usually hydrolyzed in vivo when injected in a mammal and transformed into the acid form of the compound of formula (I).

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group.

In particular the esters may be a $(C_{1-6})$alkyl ester, an unsubstituted benzyl ester or a benzyl ester substituted with at least one halogen, $(C_{1-6})$alkyl, $(C_{1-6})$alkoxy, nitro or trifluoromethyl.

Preferred Embodiments

Compounds

According to an alternative embodiment, the invention provides a compound of formula (I) or its enantiomers or diastereoisomers thereof:

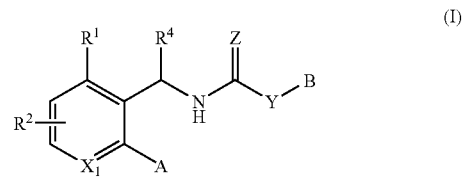

(I)

wherein $R^1$ is H, $(C_{1-6})$alkyl, halo, $(C_{1-6})$haloalkyl, $(C_{1-6})$ alkoxy, $(C_{1-6})$alkylthio, amino, $(C_{1-6})$alkylamino, di$((C_{1-6})$ alkyl)amino, $(C_{3-7})$cycloalkyl, phenyl, or 5- or 6-membered heterocycle;

$X_1$ is $CR^2$ or N;

each $R^2$ is independently selected from: H, $(C_{1-6})$alkyl, halo, $(C_{1-6})$haloalkyl, $(C_{1-6})$alkoxy, $(C_{1-6})$alkylthio, amino, $(C_{1-6})$alkylamino or di$((C_{1-6})$alkyl)amino;

A is $(C_{3-7})$cycloalkyl, $(C_6$ or $C_{10})$aryl or heterocycle, all of which being optionally substituted with:
  $(C_{1-6})$alkyl, halo, $(C_{1-6})$haloalkyl, $(C_{1-6})$alkoxy, $(C_{1-6})$ alkylthio, amino, $(C_{1-6})$alkylamino, or di$((C_{1-6})$alkyl) amino, aryl, O-aryl, S-aryl, NH-aryl, $(C_{1-6})$alkyl-aryl, heteroaryl, O-heteroaryl, S-heteroaryl, NH-heteroaryl or $(C_{1-6})$alkyl-heteroaryl;

or A is $NHR^3$ or $N(R^3)_2$ wherein
  $R^3$ is independently selected from H, $(C_{1-6})$alkyl, $(C_{3-7})$ cycloalkyl, aryl and heteroaryl;

$R^4$ is $(C_{1-6})$alkyl, $(C_{3-7})$cycloalkyl, $(C_6$ or $C_{10})$aryl, heterocycle, $(C_{1-6})$alkyl-aryl or $(C_{1-6})$alkyl-heterocycle, all of which being optionally substituted with:
 $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, aryl, heteroaryl, $(C_{1-6})$alkyl-aryl, $(C_{1-6})$alkyl-heteroaryl, $(C_{1-6})$alkoxy-aryl or $(C_{1-6})$alkoxy-heteroaryl;
or wherein the $(C_6)$aryl is fused with a saturated or unsaturated 4- to 6-membered ring optionally containing one to three heteroatoms selected from N, O, and S;
Z is O or S;
Y is $CH_2$, NH or O;
B is selected from:

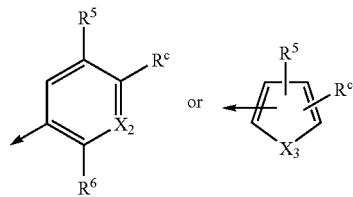

wherein $R^5$ is H, $(C_{1-6})$alkyl, $(C_{3-7})$cycloalkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl;
$X_2$ is $CR^7$ or N;
$R^6$ and $R^7$ are independently H, $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl; or, when $X_2$ is $CR^7$, $R_6$ and $R^7$ are optionally bonded together to form a saturated or unsaturated 5- or 6-membered ring optionally containing one or two heteroatoms selected from S, O and N;
$X_3$ is O, S or $NR^8$, wherein $R^8$ is H or $(C_{1-6})$alkyl; and
$R^c$ is COOH, $CONHR^9$, $SO_2NHR^9$, or tetrazolyl,
 wherein $R^9$ is H, $(C_{1-6})$alkyl, $(C_{3-6})$cycloalkyl or phenyl;
provided that $R^5$ and $R^6$ cannot both together be H and when $R^5$ or $R^6$ is H, then $R^1$ is not H, and provided that when Y is NH, $R^6$ cannot be hydroxyl or sulfhydryl;

or a pharmaceutically-acceptable salt or ester thereof.

According to a preferred embodiment, the invention provides a compound of Formula (I) or an enantiomer thereof, a diastereoisomer thereof, or a pharmaceutically-acceptable ester or salt thereof,

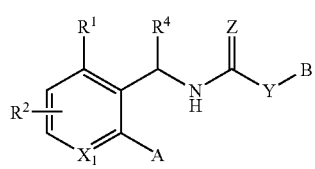

(I)

wherein $R^1$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, $(C_{3-7})$cycloalkyl, phenyl, or 5- or 6-membered heteroaryl;
$X_1$ is $CR^2$ or N;
one or both free positions on the phenyl ring may be substituted with $R^2$ and each $R^2$ is independently selected from:
 H, $(C_{1-6})$alkyl, halo, $(C_{1-6})$haloalkyl, $(C_{1-6})$alkoxy, $(C_{1-6})$alkylthio, amino, $(C_{1-6})$alkylamino and di$((C_{1-6})$alkyl)amino;

A is $(C_{3-7})$cycloalkyl, phenyl, or a 5- or 6-membered monocyclic heterocycle, each of which being optionally substituted with one or more substituents independently selected from:
 $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino and aryloxy;
or A is $NHR^3$ or $N(R^3)_2$ wherein
 each $R^3$ is independently selected from: H, $(C_{1-6})$alkyl, $(C_{3-7})$cycloalkyl, aryl and heteroaryl;
$R^4$ is $(C_{1-6})$alkyl, $(C_{3-7})$cycloalkyl, aryl, heteroaryl, $(C_{1-6})$alkyl-aryl or $(C_{1-6})$alkyl-heteroaryl, each of which being optionally substituted with one or more substituents independently selected from:
 $(C_{1-6})$alkyl, halo, $(C_{1-6})$haloalkyl, $(C_{1-6})$alkylthio, amino, $(C_{1-6})$alkylamino, di$((C_{1-6})$alkyl)amino, aryl, heteroaryl, $(C_{1-6})$alkyl-aryl, $(C_{1-6})$alkyl-heteroaryl, and $(C_{1-6})$alkoxy, wherein said $(C_{1-6})$alkoxy is optionally substituted with aryl or heteroaryl;
or $R^4$ is phenyl fused with a saturated or unsaturated 4- to 6-membered ring optionally containing one to three heteroatoms independently selected from N, O, and S;
Z is O or S;
Y is $CH_2$ or NH;
B is selected from:

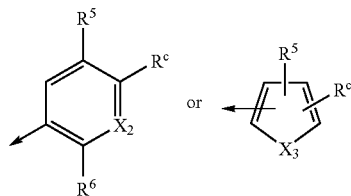

wherein $R^5$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl;
$X_2$ is $CR^7$ or N;
$R^6$ and $R^7$ are independently H, $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl;
or, when $X_2$ is $CR^7$, $R^6$ and $R^7$ are optionally bonded together to form a saturated or unsaturated 5- or 6-membered ring optionally containing one or two heteroatoms independently selected from S, O and N;
$X_3$ is O, S or $NR^8$, wherein $R^8$ is H or $(C_{1-6})$alkyl; and
$R^c$ is COOH, $CONHR^9$, $SO_2NHR^9$, or tetrazolyl;
 wherein $R^9$ is H, $(C_{1-6})$alkyl, $(C_{3-6})$cycloalkyl or phenyl;
provided that, $R^5$ and $R^6$ cannot both together be H and when $R^5$ or $R^6$ is H, then $R^1$ is not H, and provided that when Y is NH, $R^6$ cannot be hydroxyl or sulfhydryl.

More preferably, compounds of the present invention are those of formula (I) or an enantiomer thereof, a diastereoisomer thereof, or a pharmaceutically-acceptable ester or salt thereof,

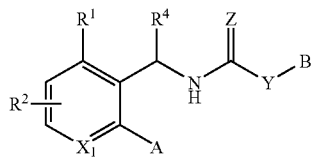

wherein $R^1$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, or di$((C_{1-6})$alkyl)amino;

$X_1$ is $CR^2$ or N;

one or both free positions on the phenyl ring may be substituted with $R^2$ and each $R^2$ is independently selected from: H or halo;

A is $(C_{3-7})$cycloalkyl, phenyl, or a 5- or 6-membered monocyclic heterocycle, each of which being optionally substituted with one or more substituents independently selected from:
$(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino and aryloxy;
or A is $NHR^3$ or $N(R^3)_2$ wherein
each $R^3$ is independently selected from: H, $(C_{1-6})$alkyl, $(C_{3-7})$cycloalkyl, aryl and heteroaryl;

$R^4$ is $(C_{1-6})$alkyl, $(C_{3-7})$cycloalkyl, aryl, heteroaryl, $(C_{1-6})$alkyl-aryl or $(C_{1-6})$alkyl-heteroaryl, each of which being optionally substituted with one or more substituents independently selected from:
$(C_{1-6})$alkyl, halo, $(C_{1-6})$haloalkyl, $(C_{1-6})$alkylthio, amino, $(C_{1-6})$alkylamino, di$((C_{1-6})$alkyl)amino, aryl, heteroaryl, $(C_{1-6})$alkyl-aryl, $(C_{1-6})$alkyl-heteroaryl, and $(C_{1-6})$alkoxy, wherein said $(C_{1-6})$alkoxy is optionally substituted with aryl or heteroaryl; or
$R^4$ is phenyl fused with a saturated or unsaturated 4- to 6-membered ring optionally containing one to three heteroatoms independently selected from N, O, and S;

Z is O;
Y is $CH_2$ or NH;
B is selected from:

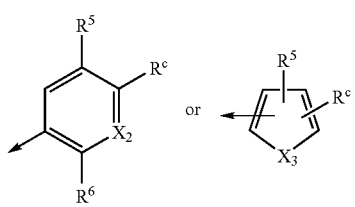

wherein $R^5$ is H, $(C_{1-6})$alkyl, halo, $(C_{1-6})$haloalkyl, $(C_{1-6})$alkoxy, $(C_{1-6})$alkylthio, $(C_{1-6})$alkylamino, or di$((C_{1-6})$alkyl)amino;

$X_2$ is N or $CR^7$;

$R^6$ and $R^7$ are independently H, $(C_{1-6})$alkyl, halo, $(C_{1-6})$haloalkyl, $(C_{1-6})$alkoxy, $(C_{1-6})$alkylthio, $(C_{1-6})$alkylamino, and di$((C_{1-6})$alkyl)amino, or, when $X_2$ is $CR^7$, $R^6$ and $R^7$ are optionally bonded together to form a saturated or unsaturated 5- or 6-membered ring, optionally containing one or two heteroatoms independently selected from S, O and N;

$X_3$ is O, S or $NR^8$, wherein $R^8$ is H or $(C_{1-6})$alkyl; and
$R^1$ is COOH or $SO_2NH_2$;

provided that, $R^5$ and $R^6$ cannot both together be H and when $R^5$ or $R^6$ is H, then $R^1$ is not H.

Most preferably, compounds of the present invention are those of formula (I) or an enantiomer thereof, a diastereoisomer thereof, or a pharmaceutically-acceptable ester or salt thereof,

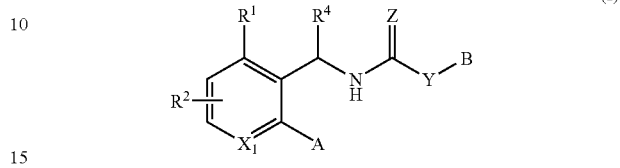

wherein $R^1$ is $(C_{1-6})$alkyl;
$X_1$ is CH;
$R^2$ is H;
A is $(C_{3-7})$cycloalkyl, phenyl, or a 5- or 6-membered monocyclic heterocycle, each of which being optionally substituted with one or more substituents independently selected from $(C_{1-6})$alkyl, halo, $(C_{1-6})$haloalkyl or aryloxy;
or A is $NHR^3$ or $N(R^3)_2$ wherein each $R^3$ is independently selected from $(C_{1-6})$alkyl, $(C_{3-7})$cycloalkyl, aryl, and heteroaryl;
$R^4$ is aryl, or heteroaryl, both optionally substituted with one or more substituents independently selected from:
$(C_{1-6})$alkyl, halo, $(C_{1-6})$haloalkyl, $(C_{1-6})$alkylthio, amino, $(C_{1-6})$alkylamino, di$((C_{1-6})$alkyl)amino, aryl, heteroaryl, and $(C_{1-6})$alkoxy, wherein said $(C_{1-6})$alkoxy is optionally substituted with aryl or heteroaryl;
or $R^4$ is phenyl fused with a saturated or unsaturated 4- to 6-membered ring optionally containing one or two heteroatoms independently selected from N, O, and S;
Z is O;
Y is $CH_2$;
B is:

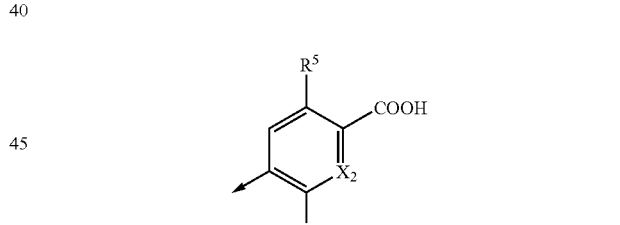

wherein $R^5$ is $(C_{1-6})$alkoxy;
$X_2$ is $CR^7$;
$R^6$ is $(C_{1-6})$alkyl, halo or $(C_{1-6})$haloalkyl, and $R^7$ is H; or $R^6$ and $R^7$ are optionally bonded together to form a saturated or unsaturated 5- or 6-membered ring, optionally containing one or two heteroatoms independently selected from S, O and N.

With respect to the compounds of formula (I), alternatively, more preferably, $R^1$ is methyl or ethyl.

Alternatively, more preferably, A is cyclohexyl, phenyl, 1-piperidinyl, 4-morpholinyl, N(H)cyclohexyl or N(CH$_3$)cyclohexyl, said cyclohexyl, phenyl, 1-piperidinyl and 4-morpholinyl being optionally mono- or di-substituted with: $(C_{1-6})$alkyl, halo, $(C_{1-6})$haloalkyl or phenoxy.

Alternatively, more preferably, A is cyclohexyl.

Alternatively, more preferably, A is phenyl.

Alternatively, more preferably, A is 1-piperidinyl or 4-morpholinyl, each optionally mono- or di-substituted with: $(C_{1-6})$alkyl, halo, $(C_{1-6})$haloalkyl or phenoxy.

Alternatively, more preferably, A is N(H)cyclohexyl or N(CH$_3$)cyclohexyl.

Alternatively, even more preferably, A is 1-piperidinyl optionally mono- or di-substituted with halo or phenoxy, and $R^1$ is H or $(C_{1-6})$alkyl.

Alternatively even more preferably, A is 1-piperidinyl and $R^1$ is H, CH$_3$, or ethyl.

Alternatively, more preferably, $R^4$ is thienyl, furanyl or naphthyl optionally substituted with one or more substituents independently selected from methoxy and $(C_{1-6})$alkyl.

Alternatively more preferably, $R^4$ is phenyl, optionally substituted with one to four substituents independently selected from: methoxy, halo, and phenyl, or $R^4$ is phenyl fused with a saturated or unsaturated 4- to 6-membered ring optionally containing one to three heteroatoms independently selected from N, O, and S.

Alternatively more preferably, $R^5$ is methoxy or ethoxy.

Alternatively preferably, $R^6$ is alkyl or halo. Alternatively even more preferably, $R^6$ is halo.

Alternatively preferably, $X_2$ is CR$^7$, wherein $R^7$ and $R^6$ are bonded together to form an unsaturated 6-membered ring which optionally contains one or two heteroatoms independently selected from S, O and N.

Alternatively more preferably, $X_2$ is CR$^7$, wherein $R^7$ and $R^6$ are bonded together to form a phenyl ring.

Alternatively preferably, compounds of the present invention are those of formula (I) wherein:
$R^1$ is H, methyl, or ethyl;
both $X_1$ and $X_2$ are CH;
one or both free positions on the phenyl ring may be substituted with $R^2$ and each $R^2$ is independently selected from: H and halo;
A is cyclohexyl, phenyl, 1-piperidyl, 4-morpholinyl, N(H)cyclohexyl, or N(CH$_3$)cyclohexyl, said cyclohexyl, phenyl, 1-piperidyl and 4-morpholinyl being optionally mono- or di-substituted with: $(C_{1-6})$alkyl, halo, $(C_{1-6})$haloalkyl, and aryloxy;
$R^4$ is aryl, or heteroaryl, both optionally substituted with one or more substituents independently selected from:
  $(C_{1-6})$alkyl, halo, $(C_{1-6})$haloalkyl, $(C_{1-6})$alkylthio, amino, $(C_{1-6})$alkylamino, di($(C_{1-6})$alkyl)amino, aryl, heteroaryl, and $(C_{1-6})$alkoxy, wherein said $(C_{1-6})$alkoxy is optionally substituted with aryl or heteroaryl;
or $R^4$ is phenyl fused with a saturated or unsaturated 4- to 6-membered ring optionally containing one or two heteroatoms independently selected from N, O, and S;
Z is O;
Y is CH$_2$ or NH;
B is:

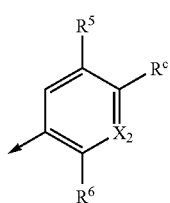

$R^5$ is methoxy or ethoxy;
$R^6$ is halo; and
$R^c$ is COOH.

Alternatively more preferably, compounds of the present invention are those of formula (I) wherein:
$R^1$ is H or methyl;
$X_1$ is CH;
$R^2$ is H;
A is 4-morpholinyl, N(H)cyclohexyl, N(CH$_3$)cyclohexyl or 1-piperidinyl, said 4-morpholinyl and 1-piperidinyl being optionally substituted with Me or phenoxy or optionally geminally difluorinated;
$R^4$ is thienyl, furanyl or naphthyl optionally substituted with one or more substituents independently selected from: methoxy and $(C_{1-6})$alkyl, or $R^4$ is phenyl optionally substituted with one to four of: methoxy, halo, or phenyl, or
$R^4$ is phenyl fused with a saturated or unsaturated 4- to 6-membered ring optionally containing one to three heteroatoms independently selected from N, O, and S;
Z is O;
Y is CH$_2$;
B is:

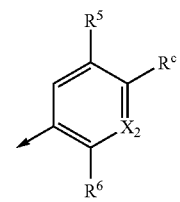

$R^5$ is methoxy;
$X_2$ is CH;
$R^6$ is bromo; and
$R^c$ is COOH.

Alternatively preferably, the compounds of the present invention are those of formula (III):

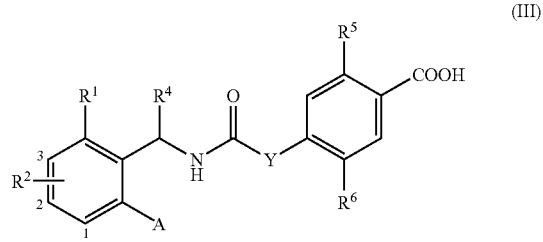

(III)

wherein $R^1$, $R^2$, A, $R^4$, Y, $R^5$, and $R^6$ are as defined herein, particularly in Table 1 below.

Alternatively more preferably, the compounds of the present invention are those of formula (IV):

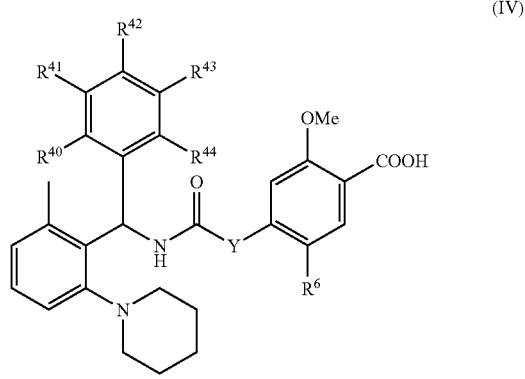

(IV)

wherein Y and $R^6$ are as defined herein, particularly in Table 2 below, and $R^{40}$, $R^{41}$, $R^{42}$, $R^{43}$, and $R^{44}$ are each independently selected from H, —$CH_3$, —$CH(CH_3)_2$—$C(CH_3)_3$, —$OCH_3$, —$N(CH_3)_2$, —$SCH_3$, —$CF_3$, chloro, fluoro, phenyl, and

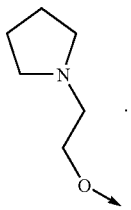

Alternatively more preferably, the compounds of the present invention are those of formula (V):

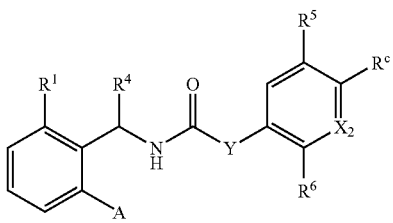

(V)

wherein $R^1$, A, $R^4$, Y, $R^5$, $R^6$, $X_2$ and $R^c$ are as defined herein, particularly in Table 3 below.

Alternatively preferably, the compounds of the present invention are those of formula (VI):

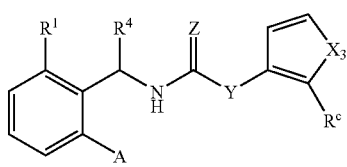

(VI)

wherein $R^1$, A, $R^4$, Z, Y, $X_3$ and $R^c$ are as defined herein, particularly in Table 4 below.

The compounds of the present invention can be synthesized as mixtures of stereoisomers and then separated into their respective single stereoisomers. All such stereoisomers are contemplated as being within the scope of the present invention.

Specific Embodiments

Included within the scope of this invention is each single compound, including its enantiomers and diastereomers, presented in Tables 1 to 4 below.

Anti-Papilloma Virus Activity

According to a second embodiment of the present invention, compounds of the present invention are useful in the treatment or prevention of papilloma virus infections, particularly human papilloma virus infection.

According to this second embodiment of the present invention, preferred compounds of formula (II) are provided:

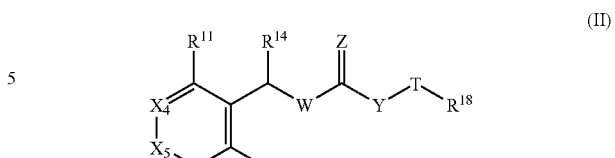

(II)

wherein $R^{11}$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, di($(C_{1-6})$alkyl)amino, $(C_{3-7})$cycloalkyl, phenyl, or 5- or 6-membered heteroaryl;

$X_4$, & and $X_6$ are independently chosen from $CR^{12}$ and N;
  each $R^{12}$ is independently selected from: H, $(C_{1-6})$alkyl, $(C_{1-6})$alkoxy, halo, $(C_{1-6})$alkylthio, $(C_{1-6})$haloalkyl, amino, $(C_{1-6})$alkylamino and di($(C_{1-6})$alkyl)amino;

$R^{13}$ is $(C_{1-6})$alkyl, $(C_{3-7})$cycloalkyl, phenyl, or 5- or 6-membered monocyclic heterocycle, wherein said $(C_{1-6})$alkyl, $(C_{3-7})$cycloalkyl, phenyl, and 5- or 6-membered monocyclic heterocycle may be optionally substituted with $R^{15}$; wherein $R^{15}$ is independently selected from H, $(C_{1-6})$alkyl, $(C_{3-7})$cycloalkyl, $(C_{1-6})$alkoxy, $(C_{1-6})$alkylthio, amino, $(C_{1-6})$alkylamino, di($(C_{1-6})$alkyl)amino, aryl, aryloxy, and heteroaryl;

or $R^3$ is —$OR^{16}$, $SR^{16}$, $NHR^{16}$ or $N(R^6)_2$, wherein
  $R^{16}$ is independently selected in each instance from H, $(C_{1-6})$alkyl, $(C_{3-7})$cycloalkyl, aryl and heteroaryl;

$R^{14}$ is H, $(C_{1-6})$alkyl, $(C_{3-7})$cycloalkyl, aryl, heteroaryl, $(C_{1-6})$alkyl-aryl and $(C_{1-6})$alkyl-heteroaryl, wherein the $(C_{1-6})$alkyl, $(C_{3-7})$cycloalkyl, aryl, heteroaryl, $(C_{1-6})$alkyl-aryl and $(C_{1-6})$alkyl-heteroaryl are optionally substituted with one or more substituents independently selected from: $(C_{1-6})$alkyl, halo, $(C_{1-6})$haloalkyl, $(C_{1-6})$alkylthio, amino, $(C_{1-6})$alkylamino, di($(C_{1-6})$alkyl)amino, aryl, heteroaryl, $(C_{1-6})$alkyl-aryl, $(C_{1-6})$alkyl-heteroaryl, and $(C_{1-6})$alkoxy, wherein said $(C_{1-6})$alkoxy is optionally substituted with aryl or heteroaryl;

or $R^{14}$ is phenyl fused with a saturated or unsaturated 4- to 6-membered ring optionally containing one to four heteroatoms independently selected from N, O, and S;

W is NH;

Y is $CH_2$, NH or O;

Z is O or S;

T is aryl, or heteroaryl, wherein said aryl, or heteroaryl are optionally substituted at one to three positions with $R^{11}$, hydroxyl or sulfhydryl; and $R^{18}$ is COOH, $COOR^{19}$, $CONHR^{19}$, $SO_2NHR^{19}$ or tetrazolyl; wherein
  $R^{19}$ is H, $(C_{1-6})$alkyl, $(C_{3-6})$cycloalkyl or phenyl.

Preferably, compounds of the present invention of formula (II) are useful in the treatment or prevention of papilloma virus infections, particularly human papilloma virus infection.

According to a preferred aspect of this second embodiment of the present invention, compounds of formula II are provided or its enantiomers or diastereoisomers thereof, in the manufacture of a medicament for the treatment or prevention of a papilloma virus infection in a mammal:

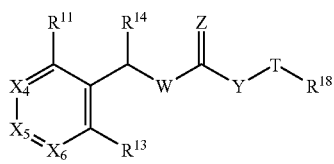

(II)

wherein $R^{11}$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, di($(C_{1-6})$alkyl)amino, $(C_{3-7})$cycloalkyl, phenyl, or 5- or 6-membered heteroaryl;

$X_4$, $X_5$ and $X_6$ are independently chosen from $CR^{12}$ and N;
  each $R^{12}$ is independently selected from: H, $(C_{1-6})$alkyl, $(C_{1-6})$alkoxy, halo, $(C_{1-6})$alkylthio, $(C_{1-6})$haloalkyl, amino, $(C_{1-6})$alkylamino and di($(C_{1-6})$alkyl)amino;

$R^{13}$ is $(C_{1-6})$alkyl, $(C_{3-7})$cycloalkyl, phenyl, or 5- or 6-membered monocyclic heterocycle, wherein said $(C_{1-6})$alkyl, $(C_{3-7})$cycloalkyl, phenyl, 5- or 6-membered monocyclic heterocycle, may be optionally substituted with $R^{15}$; wherein
  $R^{15}$ is independently selected from H, $(C_{1-6})$alkyl, $(C_{3-7})$cycloalkyl, $(C_{1-6})$alkoxy, $(C_{1-6})$alkylthio, amino, $(C_{1-6})$alkylamino, di($(C_{1-6})$alkyl)amino, aryl, aryloxy, and heteroaryl;

or $R^{13}$ is —$OR^{16}$, $SR^{16}$, $NHR^{16}$ or $N(R^6)_2$, wherein
  $R^{16}$ is independently selected in each instance from H, $(C_{1-6})$alkyl, $(C_{3-7})$cycloalkyl, aryl and heteroaryl;

$R^{14}$ is H, $(C_{1-6})$alkyl, $(C_{3-7})$cycloalkyl, aryl, heteroaryl, $(C_{1-6})$alkyl-aryl and $(C_{1-6})$alkyl-heteroaryl, wherein the $(C_{1-6})$alkyl, $(C_{3-7})$cycloalkyl, aryl, heteroaryl, $(C_{1-6})$alkyl-aryl and $(C_{1-6})$alkyl-heteroaryl are optionally substituted with one or more substituents independently selected from: $(C_{1-6})$alkyl, halo, $(C_{1-6})$haloalkyl, $(C_{1-6})$alkylthio, amino, $(C_{1-6})$alkylamino, di($(C_{1-6})$alkyl)amino, aryl, heteroaryl, $(C_{1-6})$alkyl-aryl, $(C_{1-6})$alkyl-heteroaryl, and $(C_{1-6})$alkoxy, wherein said $(C_{1-6})$alkoxy is optionally substituted with aryl or heteroaryl;

or $R^{14}$ is phenyl fused with a saturated or unsaturated 4- to 6-membered ring optionally containing one to four heteroatoms independently selected from N, O, and S;

W is NH;
Y is $CH_2$, NH or O;
Z is O or S;
T is aryl, or heteroaryl, wherein said aryl, or heteroaryl are optionally substituted at one to three positions with $R^{11}$, hydroxyl or sulfhydryl, with the proviso that T is not a pyrimidine; and
$R^{18}$ is COOH, $COOR^{19}$, $CONHR^{19}$, $SO_2NHR^{19}$ or tetrazolyl; wherein
  $R^{19}$ is H, $(C_{1-6})$alkyl, $(C_{3-6})$cycloalkyl or phenyl.

More preferably, compounds of the present invention of formula (I) are useful in the treatment or prevention of papilloma virus infections, particularly human papilloma virus infection.

Alternatively more preferably, compounds of the present invention of formula (III) are useful in the treatment or prevention of papilloma virus infections, particularly human papilloma virus infection.

Alternatively more preferably, compounds of the present invention of formula (IV) are useful in the treatment or prevention of papilloma virus infections, particularly human papilloma virus infection.

Alternatively more preferably, compounds of the present invention of formula (V) are useful in the treatment or prevention of papilloma virus infections, particularly human papilloma virus infection.

Alternatively more preferably, compounds of the present invention of formula (VI) are useful in the treatment or prevention of papilloma virus infections, particularly human papilloma virus infection.

The antiviral activity of the compounds of the present invention can be demonstrated by biochemical and biological procedures showing the inhibitory effect of the compounds on viral DNA replication.

Preferably, the compounds of the present invention described above are inhibitory against papilloma viruses, preferably human papillomavirus (HPV). More preferably the compounds are active against HPV low risk or high risk type. Even more preferably, the compounds are active against low risk type HPV (i.e. type 6 and type 11, and especially HPV type 11). Alternatively, the high-risk type is selected from the group consisting of types 16, 18, 31, 33, 35, 45, 52, or 58, preferably, type 16). Most preferably, the compounds of the invention are directed against HPV types 6 and 11, even most preferably, against HPV-11.

A biochemical procedure for demonstrating anti-papilloma virus activity for the compounds of the present invention is described in the examples hereinafter. This particular assay determines the ability of a test compound to inhibit the activity ($IC_{50}$) of HPV-11 DNA replication. More specifically, in the assay described herein, the inhibitory activity of the test compound is evaluated based on its ability to interfere with the E1-E2-DNA origin of replication interaction, thereby inhibiting initiation of viral DNA replication. The protein-protein interaction between E1 and E2 was found to be the specific target of these compounds by testing them in the assays as described in: White et al., J. Biol. Chem. 2003, 278(29), p. 26765-26772.

When a compound of the present invention or one of its therapeutically acceptable salts, is employed as an antiviral agent, it may be administered orally, topically or parenterally to mammals, e.g. humans, rabbits or mice, alone or in a vehicle comprising one or more pharmaceutically acceptable carriers, the proportion of which is determined by the solubility and chemical nature of the compound, chosen route of administration and standard biological practice.

Whether it be termed treatment or prevention, a compound of the present invention may also be used to prevent perinatal transmission of HPV from mother to baby, by administration to the mother prior to giving birth. More specifically, a compound of the present invention may be used to prevent laryngeal papillomatosis in the baby.

For oral administration, the compound or a therapeutically acceptable salt thereof can be formulated in unit dosage forms such as capsules or tablets each containing a predetermined amount of the active ingredient, ranging from about 1 to 1000 mg, alternatively ranging from about 25 to about 1000 mg, in a pharmaceutically acceptable carrier.

For topical administration, the compound may be formulated in pharmaceutically accepted vehicles containing 0.1 to 5 percent, preferably 0.5 to 5 percent, of the active agent. Such formulations can be in the form of a solution, cream or lotion.

For parenteral administration, the compound of the present invention may be administered by either intravenous, subcutaneous or intramuscular injection, in combination with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of the present invention is most desirably administered at a concentration level that will generally afford antivirally effective results without causing any harmful or deleterious side effects. An acceptable amount of the compound of the present invention would produce such a concentration level when administered to the host under treatment.

For oral administration, the compound or a therapeutically acceptable salt may be administered in the range of about 0.01 to about 15 mg per kilogram of body weight per day, with a preferred range of about 0.05 to about 10 mg per kilogram. Alternatively, the compound or a therapeutically acceptable salt may be administered in the range of about 0.5 to about 15 mg per kilogram of body weight per day, with a preferred range of about 0.5 to about 5 mg per kilogram For topical application, the compound of the present invention may be administered in a suitable formulation to the infected area of the body e.g. the skin, the genitalia, in an amount sufficient to cover the infected area. The treatment may be repeated, for example, every four to six hours until lesions heal.

For parenteral administration, the compound of the present invention may be administered at a dosage of about 0.01 mg to about 10 mg per kilogram of body weight per day, although the aforementioned variations will occur. However, a dosage level that is in the range of from about about 0.05 mg to about 5 mg per kilogram of body weight per day is most desirably employed in order to achieve effective results. Alternatively, the compound of the present invention may be administered at a dosage of about 0.1 mg to about 1 mg per kilogram of body weight per day and preferably at a dosage level of about 0.1 mg to about 0.5 mg per kilogram of body weight per day.

Although the formulations disclosed herein are indicated to be effective and relatively safe medications for treating or preventing papilloma viral infections, the possible concurrent administration of these formulations with other medications or agents to obtain beneficial results is also contemplated. Such other medications or agents include TCA, podophyllin, podofilox, Interferon or Imiquimod.

In addition to the above-mentioned antiviral agents, the compounds according to the invention may also be used post-cryotherapy or post-surgery to avoid recurrence or in combination with any other treatment for physically removing warts.

Methodology and Synthesis

Numerous methodologies for the preparation of compounds of the present invention for use in the treatment or prevention of papilloma virus infections, will be readily recognized by a person skilled in the art.

The compounds of the present invention can be synthesized as racemic mixtures and then separated into their individual stereoisomers using a variety of routes which will be readily recognized by those skilled in the art.

In general, the left hand side fragment of the compounds of the present invention may be prepared as a nitrile or as an aldehyde bearing the A, $R^1$ and $R^2$ groups as follows:

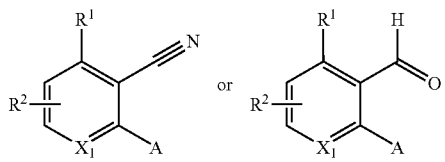

The A group of the left-hand side fragment is typically introduced onto the aromatic skeleton of the left-hand side fragment by nucleophilic substitution of the halo-substituted aromatic ring (see Example 1 below).

The amine intermediate fragment bearing A, $R^1$, $R^2$ and $R^4$ groups may be prepared by a variety of routes which will be readily recognized by those skilled in the art. The general structure of the amine intermediate fragment is as follows:

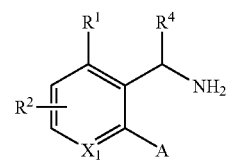

When the left-hand side fragment is a nitrile, the amine intermediate fragment may be prepared by formation of an intermediate imine complex upon introduction of the $R_4$ group via nucleophilic attack on the nitrile, followed by reduction of the imine intermediate to the desired amine product (see Example 7, below). When the left-hand side fragment is an aldehyde, the intermediate amine fragment may be formed by first making a phosphorylamine which is subsequently reacted with a lithium anion of the $R_4$ group to give the phosphorylamine intermediate. Hydrolysis of the latter leads to the desired amine product (see Example 9, below).

Coupling of the right-hand side fragment to the amine intermediate may be achieved by a variety of routes which will be readily recognized by those skilled in the art. When the invention covers compounds of formula (I) where Y is $CH_2$ the amine intermediate is coupled to an appropriate carboxylic acid as follows:

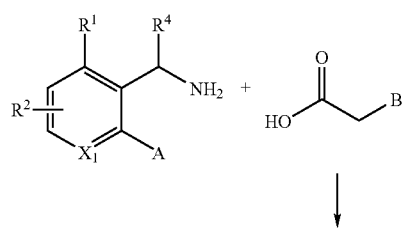

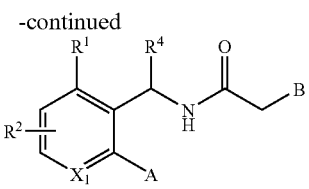

Such coupling will be readily recognized by persons skilled in the art. When the invention covers compounds of the formula (I) where Y is NH, the urea functionality may be achieved by coupling of the amine intermediate to an appropriate right-hand side aniline fragment by a variety of routes which will be readily recognized by those skilled in the art, including by way of the isocyanate intermediate as follows:

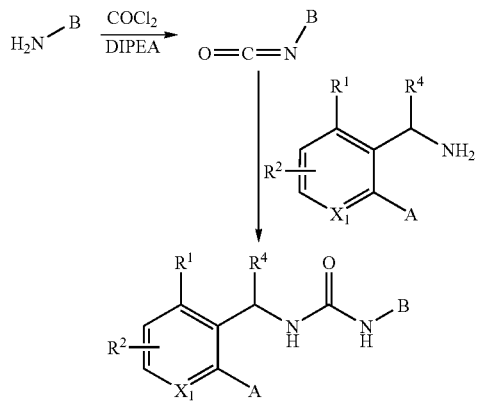

EXAMPLES

The present invention is illustrated in further detail by the following non-limiting examples.

Abbreviations or symbols used herein include the following:

AcOH: acetic acid;
DEAD: diethyl azodicarboxylate;
DIAD: diisopropylazodicarboxylate;
DIPEA: diisopropylethylamine;
DMAP: 4-(dimethylamino)pyridine;
DMSO: dimethylsulfoxide;
DMF: dimethylformamide;
ES⁺ MS: electron spray positive mode mass spectrometry;
Et: ethyl;
EtOAc: ethyl acetate;
Et₂O: diethyl ether;
HATU: [O-(7-azabenzotriazol-1-yl)-1,2,3,3,tetramethyluroniumhexafluorophosphate];
HMPA: hexamethyl phosphoramide;
HPLC: high performance liquid chromatography;
i-Pr: isopropyl;
LDA: lithium diisopropylamide;
Me: methyl;
MeOH: methanol;
MeCN: acetonitrile;
Ph: phenyl;
RBF: round bottom flask;
RT: room temperature;
TBE: tris-borate-EDTA;
t-Bu: tert-butyl;

TBTU: 2-(1H-benzotriazol-1-yl)-N,N,N',N'-tetramethyluronium tetrafluoroborate;
TFA: trifluoroacetic acid;
THF: tetrahydrofuran;
TLC: thin layer chromatography.

The present invention is illustrated in further detail by the following non-limiting examples.

Left Hand-Side Fragments of Inhibitors

Example 1

Synthesis of 2-methyl-6-piperidin-1-ylbenzonitrile (1b)

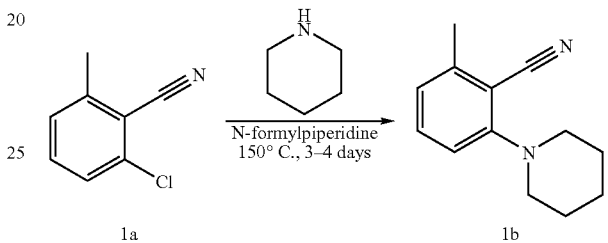

2-Methyl-6-piperidin-1-ylbenzonitrile (1 b) was prepared according to the method described by Grell, W. *J. Med. Chem.* 1998, 41, 5219. A mixture of 2-chloro-6-methylbenzonitrile (1a, 8.5 g), piperidine (16.6 mL, 3 eq) and N-formyl piperidine (12.5 mL) was heated in an oil bath at 150° C. under N₂. After a period of 4 days, HPLC indicated complete conversion of starting materials to product. The reaction mixture was cooled to RT, dissolved in 100 mL of EtOAc, washed with water, 10% HCl, and NaHCO₃ (sat), dried over anhydrous MgSO₄ and treated with charcoal. The product was concentrated under vacuum to give the crude product (1 b) as pale yellow oil (12.01 g); C₁₈ reversed phase HPLC indicated 88% homogeneity at 220 nm. This crude product was purified by flash column chromatography (hex-EtOAc, 1:0 to 20:1 to 10:1) to afford 2-methyl-6-piperidin-1-ylbenzonitrile (1 b) as colorless oil which solidifies upon standing (~80% yield).

Example 2

Synthesis of 2-piperidin-1-yl-6-thiophen-3-ylbenzonitrile (2c)

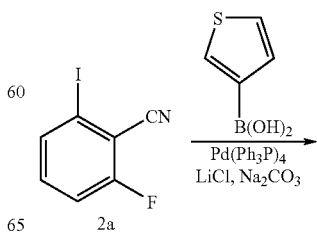

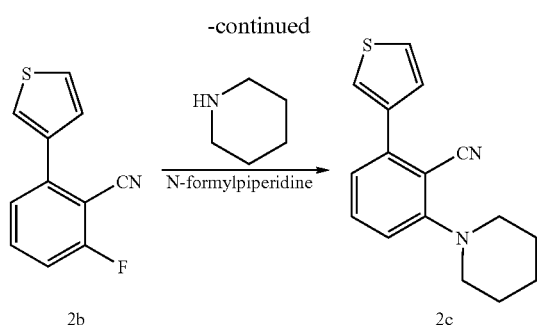

A mixture of 2-fluoro-6-iodobenzonitrile (2a, 1.5 g, 6.1 mmol), 3-thiopheneboronic acid (0.99 g, 7.7 mmol), LiCl (0.51 g, 12.0 mol), Na$_2$CO$_3$ (1.6 g, 15.1 mmol), toluene (10 mL), ethanol (10 mL) and H$_2$O (7 mL) was degassed and de-oxygenated under argon while stirring for 45 min. The Pd(Ph$_3$P)$_4$ catalyst (0.28 g, 0.24 mmol) was added and the mixture was heated to 80° C. for ~15 hours. The reaction mixture was cooled to RT and the residue was partitioned between H$_2$O (40 mL) and EtOAc (40 mL). The aqueous layer was extracted two more times with EtOAc and the combined organic layers were dried over anhydrous sodium sulfate and evaporated to dryness under reduced pressure to give compound 2b, which was reacted with piperidine using the procedure described in Example 1. The pure product 2-piperidin-1-yl-6-thiophen-3-ylbenzonitrile (2c) (~1.2 g, >98% yield) was obtained after flash column chromatography.

Example 3

Synthesis of 2-methyl-6-piperidin-1-ylbenzaldehyde (3c)

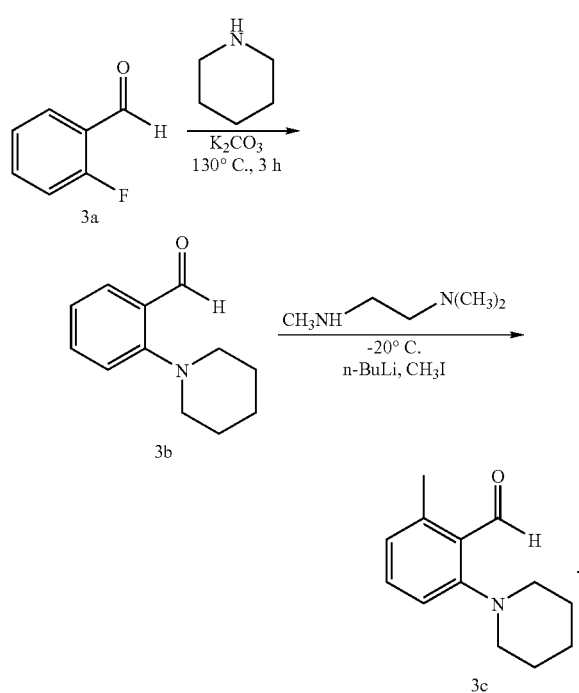

To a solution of the aldehyde 3a (20 g, 161.1 mmol) in dry DMF (160 mL), piperidine (19.1 mL, 193.4 mmol, 1.2 eq) and potassium carbonate (26.73 g, 193.4 mmol, 1.2 eq) were successively added. The suspension was heated at 130° C. for 3 h. The reaction mixture was then poured into cold water and acidified with citric acid up to pH 5. The aqueous layer was extracted 3X with EtOAc and the combined organic extract was successively washed with water, saturated NaHCO$_3$ and brine. After drying the organic extract over MgSO$_4$, filtration and concentration, the desired 2-piperidinobenzaldehyde 3b was isolated as a red oil (28.23 g, 92% yield).

To a solution of N,N,N'-trimethylethylenediamine in dry THF (110 mL), cooled to −20° C., n-BuLi (27.3 mL of a 1.6 M solution in hexane, 43.68 mmol, 1.0 eq) was added dropwise. After 15 min, a solution of 2-piperidin-1-ylbenzaldehyde 3b (8.0 g, 42.27 mmol) in THF (20 mL) was added slowly while maintaining the temperature at −20° C. After an additional 15 min, additional n-BuLi (79.25 mL of a 1.6 M solution in hexane, 126.8 mmol, 3.0 eq) was slowly added. The reaction mixture was maintained at −20° C. for 90 h using a cryocool apparatus and then cooled to −78° C. for the addition of methyl iodide (15.8 mL, 253.8 mmol, 6.0 eq). The cooling bath was removed after the addition and the work-up was carried out once the reaction mixture was at RT. The mixture was poured into a cold solution of saturated NH$_4$Cl and extracted 3X with EtOAc. The combined organic layer was washed with brine, dried over anhydrous MgSO$_4$, filtered and concentrated to afford a brown oil which was purified by flash chromatography using a mixture consisting of 5% EtOAc-95% hexane as eluent. The desired 2-methyl-6-piperidin-1-ylbenzaldehyde 3c was isolated as pale yellow oil (3.74 g, 43% yield).

Example 4

Synthesis of 2-methyl-6-(4-phenoxypiperidin-1-yl)benzonitrile (4c)

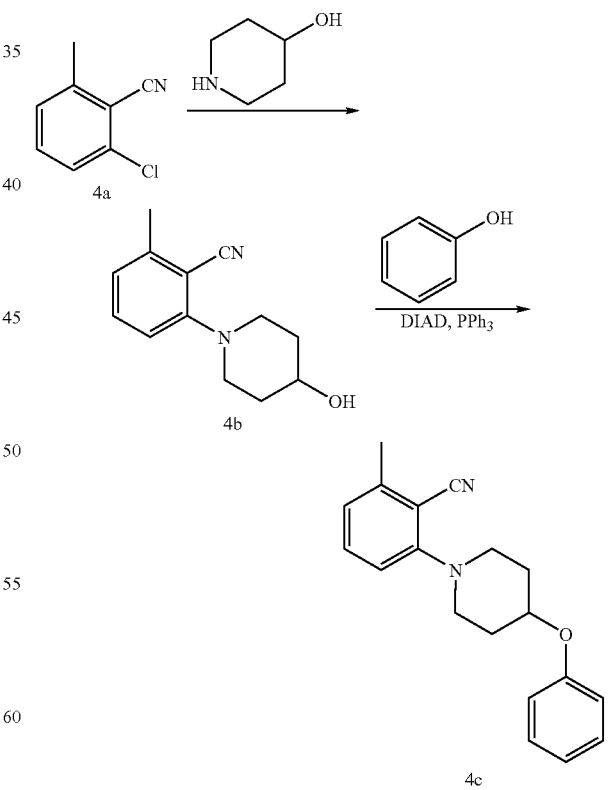

A mixture of the nitrile 4a (1.25 g, 8.25 mmol) and 4-hydroxypiperidine (2.50 g, 24.7 mmol) was heated in a vial to 180° C. for 2 hours. The reaction mixture was diluted with EtOAc and the organic layer was washed with 0.1 N HCl, followed by saturated aqueous NaHCO₃ and brine. The organic layer was dried over anhydrous MgSO₄ and concentrated to dryness. The residue was purified by flash column chromatography, using a solvent gradient from 20% to 100% EtOAc in hexane, to give the pure desired intermediate alcohol 4b as a white solid (1.44 g).

A sample of the above alcohol intermediate (4b, 153 mg, 0.71 mmol) was dissolved in anhydrous THF and the solution was cooled to 0° C. Triphenylphosphine (278 mg, 1.1 mmol) and diisopropylazodicarboxylate (DIAD, 209 µL, 1.06 mmol) were added and the mixture was stirred at 0° C. for 10 min before adding phenol (133 mg, 1.4 mmol). The ice bath was then removed and the reaction mixture was stirred at RT overnight. The THF solvent was first evaporated under vacuum, the residue was re-dissolved in EtOAc and washed with H₂O, 1N NaOH, H₂O and brine. The organic layer was dried over anhydrous MgSO₄ and concentrated to dryness. The crude mixture was purified by flash column chromatography, using a solvent gradient from 5% to 20% EtOAc in hexane, to isolate the pure 2-methyl-6-(4-phenoxypiperidin-1-yl)benzonitrile product 4c as a white solid (180 mg, 87% yield).

Example 5

Synthesis of 2-cyclohexyl-6-methylbenzonitrile (5b)

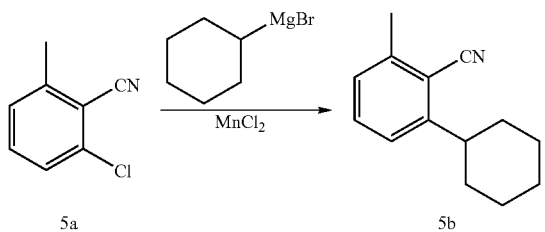

2-Cyclohexyl-6-methylbenzonitrile was prepared according to the method of G. Cahiez, F. Lepifre and P. Ramiandrasoa, *Synthesis,* 1999, No. 12, 2138-2144. To a mixture of nitrile 5a (303.2 mg, 2.00 mmol) and MnCl₂ tetrahydrate (finely ground, 39.6 mg, 0.2 mmol, 0.1 eq) in dry THF (5 mL) at 0° C., the Grignard reagent cyclohexylmagnesium bromide (4 mL, 1.0 M solution in THF, 4.0 mmol, 2.0 eq) was added slowly. The reaction mixture was stirred at 0° C. for 2 hours and then quenched by the addition of a saturated aqueous NH₄Cl solution. The aqueous layer was extracted with diethyl ether (3x) and the combined organic layers were successively washed with water and brine. After drying over MgSO₄, filtration and concentration, the desired material, 2-cyclohexyl-6-methylbenzonitrile 5b, was isolated (168 mg).

Example 6

Synthesis of 2-ethyl-6-piperidin-1-ylbenzonitrile (6b)

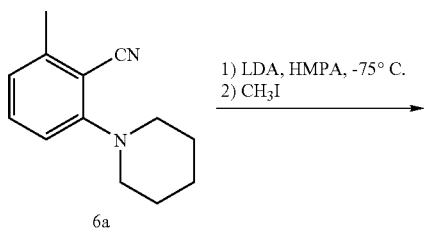

-continued

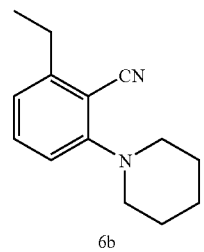

In an argon-dried 50 mL 3-neck round bottom flask fitted with a magnetic stirring bar, thermometer and septa with argon inlet, anhydrous THF (20 mL) and DIPEA (0.84 mL, 6 mmol, 1.2 eq) were introduced consecutively. The mixture was cooled to −30° C. and 1.6 M n-BuLi solution (3.75 mL, 6 mmol, 1.2 eq) was added dropwise via syringe. After 30 min stirring at −30° C. the in situ generated LDA solution was cooled to −76° C. and HMPA (1.3 mL, 7.5 mmol, 1.5 eq) was added, followed by a solution of 2-methyl-6-piperidinyl-1-ylbenzonitrile (6a, 1.0 g, 5 mmol) in THF (5 mL) which caused a dark coloration of the reaction mixture. The reaction was stirred at −76° C. for 2 h and MeI (0.4 mL, 6.5 mmol, 1.3 eq) was added. Immediately the dark brown solution became slightly yellow, indicating that the alkylation reaction was complete. The reaction was allowed to warm up to RT, quenched with saturated NH₄Cl solution (20 mL) and the product was extracted with diethyl ether (3×30 mL). The combined organic extracts were washed with brine, dried over anhydrous sodium sulfate and the solvent was removed under reduced pressure. The crude product was purified by flash chromatography (eluted with 5% EtOAc in hexane) to give pure 2-ethyl-6-piperidin-1-ylbenzonitrile (6b, 0.88 g, 82% yield).

Amine Intermediate Fragment of Inhibitors

Example 7

Synthesis of 1-(2-methyl-6-piperidin-1-yl-phenyl)-1-phenyl-methylamine (7c)

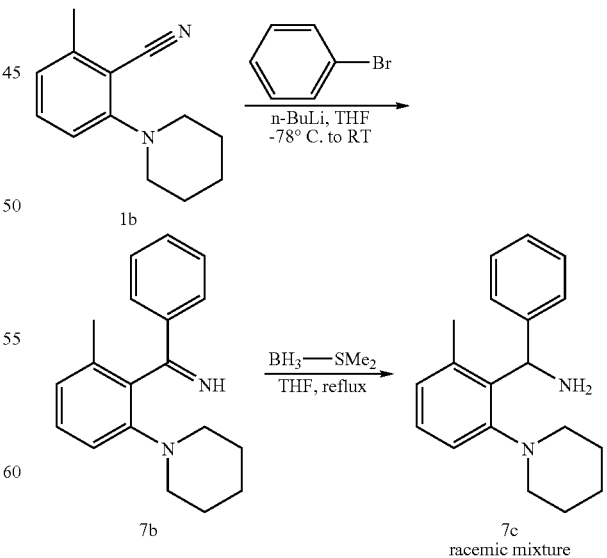

A solution of bromobenzene (118 mg, 0.75 mmol) in dry THF (2 mL) was cooled to −78° C. and n-BuLi (1.6 M in hexane, 0.375 mL, 0.6 mmol) was added. The reaction mixture was stirred for 30 min at −78° C., then a solution of nitrile 1b (100 mg, 0.5 mmol, in 1 mL of THF) was added and stirring was continued at −78° C. for 5 more min. The reaction mixture was allowed to warm up to RT and stirring was continued for 2 hours. The reaction was quenched with the addition of saturated NH$_4$Cl (1.5 mL) and NH$_4$OH (1.5 mL) followed by stirring for 30 min. The organic layer was separated, the aqueous layer was re-extracted with EtOAc and the combined organic layers were washed with brine, dried over anhydrous MgSO$_4$ and concentrated under vacuum to give the crude imine intermediate 7b which was used in the next step without purification.

The crude imine intermediate 7b was re-dissolved in THF (3 mL), BH$_3$ SMe$_2$ (10M, 100 μL, 1.0 mmol) was added and the reaction mixture was heated to reflux for 6 hours. The solvent was removed under vacuum, the crude residue was acidified with 3 mL of 1N HCl and washed with EtOAc (2×10 mL). The pH of the aqueous layer was adjusted to 8-10 by addition of 10N NaOH and the product was extracted into EtOAc (2×10 mL). The combined organic layers were washed with brine, dried over MgSO$_4$ and evaporated to dryness to give a pale yellow oil. This crude product was purified by flash column chromatography (using a gradient from hexane-EtOAc 10:1 to 5:1 then CH$_2$Cl$_2$-MeOH 1:0 to 10:1) to provide 7c as a racemic mixture. The yield varied from 35-70%. ES$^+$ MS m/z: 281 (M+H)$^+$ Example 8

Synthesis of 1-(4-methoxyphenyl)-1-(2-methyl-6-piperidin-1-ylphenyl)methylamine (8c)

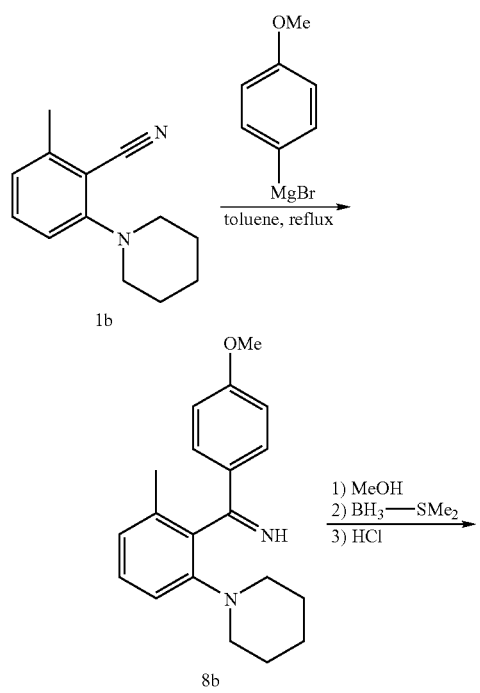

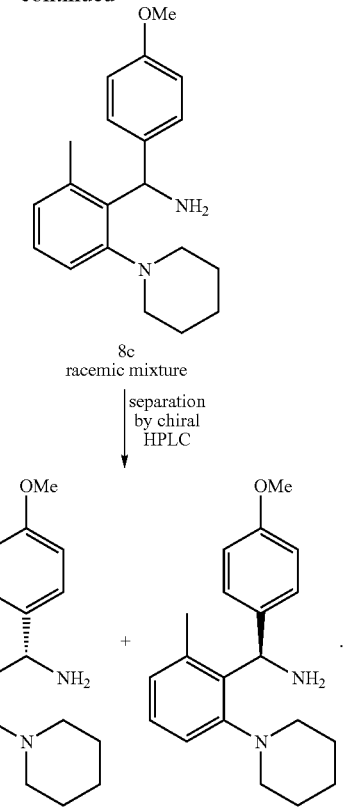

A dry 25 mL 3-neck flask with a stirring bar and condenser was flushed with argon. A solution of nitrile 1b (0.33 g, 1.43 mmol) in toluene (10 mL) was added and the volume of the solution was reduced to ~1/5 by distilling out some of the toluene. The solution was cooled to RT and the Grignard reagent 4-methoxyphenyl-magnesium bromide (5.75 mL, 0.5 M in THF) was added. The reaction mixture was heated to reflux and the THF was first removed by distillation before leaving the mixture to reflux, while stirring, for approximately 15 hours. The reaction was cooled back to RT, BH$_3$ SMe$_2$ (1.0 M, 3 mL) was added and the mixture was heated to reflux for 15 hours. The solvent was removed under vacuum, 10% aqueous HCl was added (20 mL) and the mixture was heated again to reflux for 2.5 hours. The reaction mixture was first extracted with diethyl ether (2×10 mL), the aqueous layer was neutralized with NH$_4$OH and extracted with EtOAc (3×15 mL). The EtOAc layer was dried over anhydrous MgSO$_4$ and evaporated to dryness. The residue was purified by flash column chromatography, using 1-2% CH$_3$OH in CH$_2$Cl$_2$, to give the racemic products 1-(4-methoxy-phenyl)-1-(2-methyl-6-piperidin-1-yl-phenyl)-methylamine 8c as a yellow oil (0.44 g, 90% yield).

Chiral HPLC was utilized to afford the enantiomerically-enriched samples. Separation of the two enantiomers was achieved by preparative scale HPLC, using a ChiralCel OD column (2.00 cm×25 cm), 40% aqueous CH$_3$CN (containing 0.06% TFA) as eluting solvent at a flow rate of 7 ml/min. The enantiomer of the first eluting amine had an e.e. value of 98.8% as determined by analytical chiral HPLC, and was used to synthesize potent inhibitors of HPV (eutomer). Compounds synthesized with the enantiomer corresponding to the second eluting peak were significantly less active as inhibitors of HPV (distomer).

Example 9

Synthesis of 1-(2-Methyl-6-piperidinylphenyl)-1-[4-(2-pyrrolidin-1-ylethoxy)phenyl]methylamine (9d)

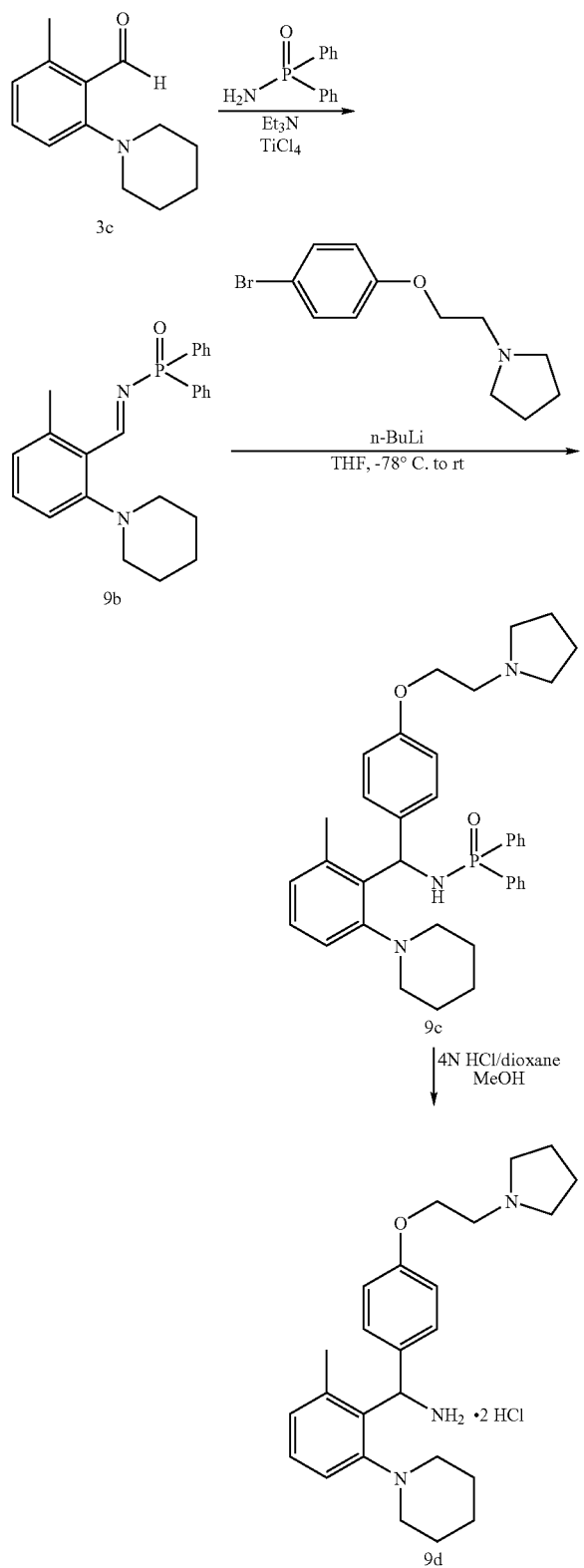

To a solution of aldehyde 3c (1.17 g, 4.92 mmol), diphenylphosphinamide (1.068 g, 4.92 mmol, 1.0 eq), and triethylamine (2.07 mL, 14.84 mmol, 3.0 eq) in dry $CH_2Cl_2$ (6 mL) at 0° C. was added dropwise a 1.0 M $TiCl_4$ solution in dichloromethane (2.68 mL, 2.68 mmol). The mixture was stirred for 10 min. at 0° C. and then overnight at RT. The heterogeneous mixture was filtered through a pad of Celite. The filtrate was concentrated and the residue was treated twice with ether, and the triethylammonium hydrochloride salt that precipitated each time was removed by filtration. After concentration the desired imine 9b was isolated as a yellow oil (1.532 g, 3.80 mmol, 77% yield). The desired imine showed a characteristic doublet of ~32 Hz coupling constant between the imine C—H and P.

To 1-[2-(4-bromophenoxy)ethyl]pyrrolidine (41.4 μL, 0.2 mmol, 2.0 eq) in dry THF (500 μL) at −78° C. was slowly added n-BuLi (230 μL, 0.368 mmol, 1.8 eq). After 1 h the crude imine 9b (40.2 mg, 0.10 mmol) in THF (250 μL) was added. After the addition was completed, the reaction mixture was allowed to warm-up to RT and stirred at this temperature for 15 min. A saturated aqueous solution of $NH_4Cl$ was added (600 μL) and the aqueous layer was extracted with EtOAc (3X). The combined organic extract was washed with brine, dried over $MgSO_4$, filtered and concentrated to give the crude protected amine 9c. This crude intermediate was dissolved in absolute methanol (500 μL) and a solution of 4N HCl in dioxane (500 μL) was added. The reaction mixture was stirred at RT overnight and concentrated to dryness to give the desired hydrochloride salt of 1-(2-methyl-6-piperidinylphenyl)-1-[4-(2-pyrrolidin-1-ylethoxy)phenyl]methylamine 9d, which was used in the synthesis of inhibitors without further purification.

Right-Hand Side Fragments of Inhibitors where $X_2$=CH

Example 10

Synthesis of methyl 5-bromo-4-carboxymethyl-2-methoxybenzoate (10d)

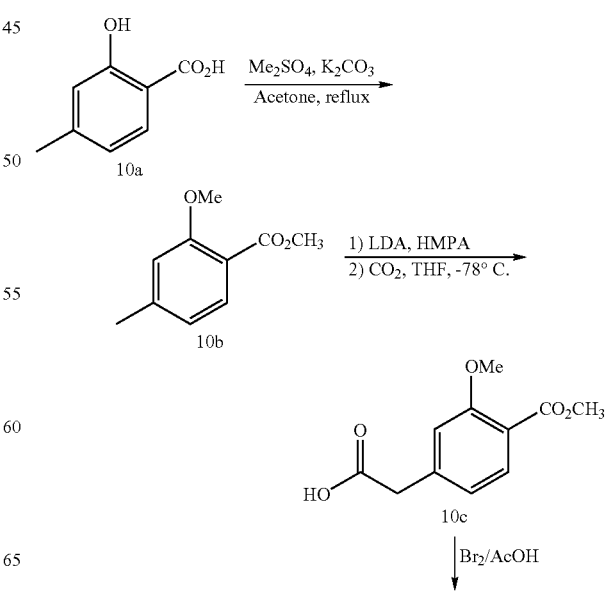

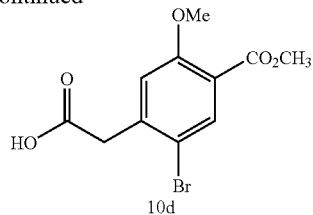

Methyl 5-bromo-4-carboxymethyl-2-methoxybenzoate was synthesized according to the method described in WO 01/35900. A 1 L 3-neck RBF, fitted with a dropping funnel, a condenser and a magnetic stirring bar was charged with 4-methylsalicylic acid 10a (50 g, 0.33 mol), $K_2CO_3$ (91.1 g, 0.66 mol, 2 eq) and dry acetone (500 mL). This mixture was heated under reflux while dimethylsulfate (112.3 g, 0.891 mol, 2.7 eq) was added dropwise. The reaction mixture was refluxed for ~14 h (TLC indicated that the reaction was completed). The inorganic salts were filtered off and the THF filtrate was evaporated under reduced pressure to obtain a yellow oil. This residue was dissolved in 400 mL MeOH and a solution of conc. $NH_4OH$ (115 mL) was added. The resulting mixture was stirred at RT for 30 min. The MeOH was then distilled off and the residue was diluted with water (500 mL) and the oily product was extracted with diethyl ether (3×300 mL). The combined organic extracts were dried over sodium sulfate and the diethyl ether was removed under vacuum to give pure methyl 2-methoxy-4-methylbenzoate 10b as a yellow oil (57 g, 96% yield).

A dry 2 L 3-neck RBF fitted with an argon inlet, a thermometer, a magnetic stirring bar and a septum was charged with THF (220 mL) and diisopropylamine (54.6 mL, 0.39 mol, 1.2 eq). The resulting mixture was cooled to –50° C. and a solution of 2.5 M n-BuLi (156 mL, 0.39 mol, 1.2 eq) was added slowly via cannula. After 30 min of stirring at –50° C., the solution of LDA generated was cooled to –78° C. and HMPA (67.8 mL, 0.39 mol, 1.2 eq) was added, followed by a solution of methyl 2-methoxy-4-methylbenzoate 10b (57 g, 0.32 mol) in THF (220 mL), while maintaining the temperature at –78° C. The reaction mixture was stirred two more hours at –78° C., and then cannulated into a flask containing 100 g dry ice and THF (200 mL). After 30 min stirring at –78° C., the reaction mixture was allowed to warm up slowly to RT and then poured into water (1.5 L). The organic layer was separated and the aqueous layer was further extracted with ether (3×1 L). The water layer was acidified with a solution of 10% $H_2SO_4$ (150 mL) and the reaction product was extracted into $CH_2Cl_2$ (3×1.5 L). The combined organic extracts were dried over anhydrous $Na_2SO_4$, the solvent was removed under reduced pressure and the crude product was purified by flash chromatography (eluent EtOAc: hexane 3:7), followed by recrystallization from $CH_2Cl_2$:hexane 1:1 to afford pure methyl 4-carboxymethyl-2-methoxybenzoate 10c (38.8 g, 54.7% yield).

Methyl 4-carboxymethyl-2-methoxybenzoate 10c (12.7 g, 0.0567 mol) was dissolved in glacial AcOH (100 mL) and bromine (3.2 mL, 0.0624 mol, 1.1 eq) was added drop wise via a syringe, while maintaining the internal temperature between 20-25° C. After stirring for 4 h at RT, the AcOH was evaporated and the orange oil co-evaporated twice with toluene to give an orange solid. This material was triturated with $CH_2Cl_2$ and some of the precipitated product was removed by filtration. The rest of the product which remained in the filtrate was then concentrated, loaded on a silica gel column and eluted with 1% AcOH in EtOAc:hexane (6:4 ratio). The product was further purified by a second chromatography and re-crystallization from EtOAc:hexane to give pure methyl 5-bromo-4-carboxymethyl-2-methoxybenzoate as white solid 10d (total amount 9 g, 52% yield).

Example 11

Synthesis of methyl 4-carboxymethylnaphthalene-1-carboxylate (11c)

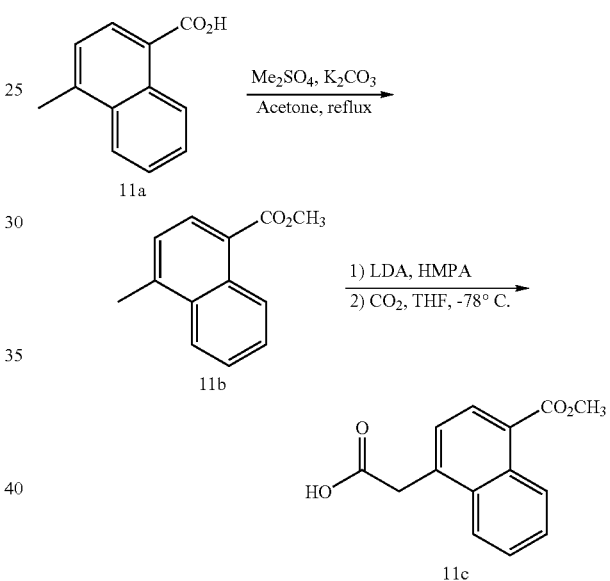

Synthesis of intermediate 4-carboxymethylnaphthalene-1-carboxylic acid methyl ester 11c was carried out following the same experimental procedures as those previously described for the synthesis of the intermediate methyl 4-carboxymethyl-2-methoxybenzoate in Example 10.

Example 12

Synthesis of (2-bromo-5-methoxy-4-sulfamoylphenyl)acetic acid (12f)

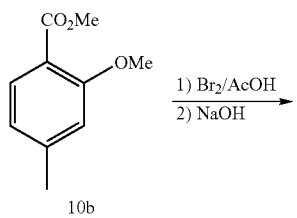

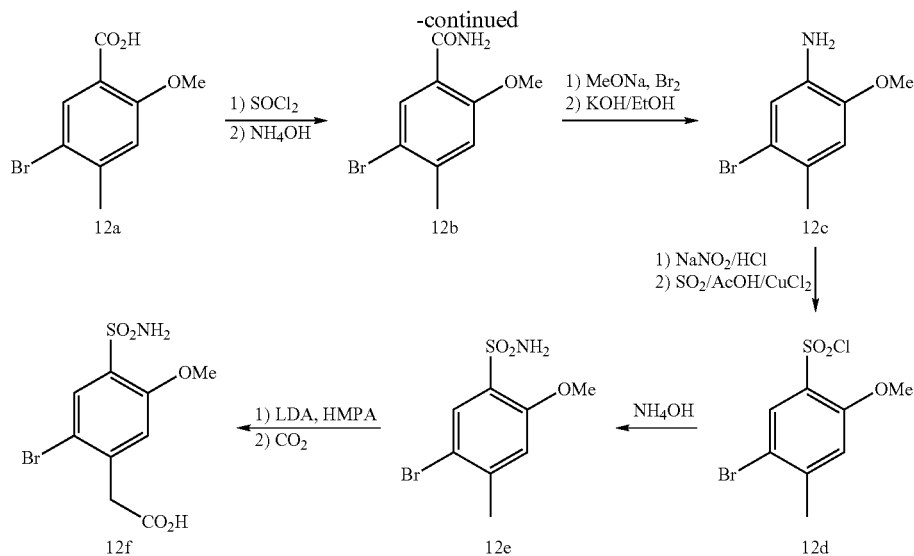

A 250 ml 3-neck RBF fitted with a magnetic stirring bar, a thermometer and a dropping funnel was charged with methyl 2-methoxy-4-methylbenzoate 10b (10 g, 0.056 mol) and AcOH (70 mL). To this solution bromine (3 mL, 0.06 mol) was added drop-wise while maintaining the reaction temperature below 25° C. When bromine addition was complete, the reaction mixture was stirred at RT for 2 hours, then poured into 600 mL of cold water and the pH was adjusted to 8-9 with $Na_2CO_3$. The crude product was extracted with $Et_2O$ (3×300 mL), the combined extracts washed with brine, dried over sodium sulfate and the solvent was removed under vacuum to give methyl 5-bromo-2-methoxy-4-methylbenzoate as an orange oil, which solidified on standing (14.3 g, 99% yield, >90% purity by $^1H$ NMR).

Methyl 5-bromo-2-methoxy-4-methylbenzoate (11.64 g, 0.045 mol) was dissolved in a mixture of $EtOH:H_2O$ (1:1 ratio, 150 mL), NaOH (5.8 g, 0.145 mol) was added and reaction mixture was refluxed for 30 min. The EtOH solvent was removed from the mixture by distillation which leads to precipitation of the desired product as its sodium salt. The residue was diluted with $H_2O$ (75 mL) and the pH was adjusted to ~2 with concentrated HCl. The precipitate was collected by filtration, washed with $H_2O$ (3×50 mL) and air dried to give pure 5-bromo-2-methoxy-4-methylbenzoic acid 12a (9 g, 82% yield) as a beige solid.

A mixture of 5-bromo-2-methoxy-4-methylbenzoic acid 12a (9 g, 0.037 mol), thionyl chloride (5 ml, 0.069 mol) and benzene (90 mL) was heated to reflux for 4 hours, then evaporated to dryness at reduced pressure. The residue of the chloroanhydride intermediate was dissolved in dry benzene (40 mL) and poured slowly into an ice cooled flask containing 150 mL of concentrated ammonium hydroxide solution. The reaction mixture was then stirred for 1 hour at RT and the solid material which precipitated was collected by filtration, washed with water (3×25 mL), benzene (2×20 mL) and air dried to afford pure 5-bromo-2-methoxy-4-methylbenzamide 12b (8.5 g, 95% yield) as beige solid.

A 250 ml 3-neck RBF fitted with a magnetic stirring bar, a thermometer, a dropping funnel and a condenser was charged with 5-bromo-2-methoxy-4-methylbenzamide 12b (6 g, 24.6 mmol), anhydrous MeOH (40 mL) and 25% NaOMe solution in MeOH (21 mL, 98.4 mmol). This slurry was cooled to 5° C. and bromine (1.4 mL, 27.1 mmol) was added drop wise causing an exothermic reaction and the formation of a cloudy solution. The reaction mixture was stirred for 30 min at RT, and then heated to reflux for 1 hour. The solvent was removed under vacuum, the residue was re-dissolved in EtOH (50 mL) and KOH (5.5 g, 98.4 mmol) was added. The mixture was allowed to react under reflux for 16 hours in order to hydrolyze the intermediate methylcarbamate. Then the reaction mixture was diluted with $H_2O$ (300 mL) and the product was extracted into $Et_2O$ (3×100 mL). The combined organic layers were filtered through a pad of silica gel and evaporated to dryness to give 5-bromo-2-methoxy-4-methylaniline 12c (4.8 g, 90% yield) pure by $^1H$ NMR as a light brown solid.

A suspension of 5-bromo-2-methoxy-4-methylaniline hydrochloride [formed from the reaction of 5-bromo-2-methoxy-4-methylaniline (4.32 g, 20 mmol) with conc. HCl (20 ml)] was cooled to 0° C. and an aqueous solution of $NaNO_2$ (1.224 g, 24 mmol in 5 mL $H_2O$) was added slowly, keeping the reaction temperature below 5° C. When addition of the nitrite was complete, the reaction mixture was stirred for 30 min at 0° C., then poured into a previously prepared mixture containing 30% $SO_2$ in AcOH (30 mL), a solution of $CuCl_2 2H_2O$ (5.13 g, 30 mmol) in 15 mL $H_2O$ and benzene (20 mL). The reaction mixture was heated slowly to 35° C., at which point the evolution of nitrogen gas was observed. When gas evolution had stopped, the reaction mixture was diluted with water (200 mL), the organic layer was separated, washed with an aqueous solution of saturated $NaHCO_3$, dried over $Na_2SO_4$ and evaporated to dryness to give the crude sulfonylchloride 12d as a brown oil (~3 g). This intermediate was dissolved in hexane (20 mL), a solution of concentrated $NH_4OH$ (20 mL) was added and reaction mixture was stirred vigorously at RT overnight. The brown solid formed was collected by filtration and treated with 10% KOH solution (20 mL). Any insoluble impurities were removed by filtration and the filtrate was acidified to give a beige precipitate which was filtered, washed with water and air dried to give the pure product 5-bromo-2-methoxy-4-methylbenzenesulfonamide 12e (0.586 g, 10.4% overall yield).

A dry 25 mL 3-neck RBF, fitted with a magnetic stirring bar, a thermometer and septum with Ar inlet was charged with 5-bromo-2-methoxy-4-methylbenzene-sulfonamide 12e (0.586 g, 2.1 mmol), anhydrous THF (5 mL) and HMPA (0.37 mL, 2.1 mmol). The mixture was cooled to −75° C. and a 2.0 M solution of LDA (4.2 mL, 8.4 mmol) was added drop wise via a syringe. The reaction mixture was stirred at −75° C. for 1.5 hours and then cannulated into a flask containing 20 g of dry ice and 5 mL THF and left to warm up slowly to RT. The solvent was removed under reduced pressure and H₂O (20 mL) was added to the residue. At this point, some of the unreacted starting material precipitated and was removed by filtration. The filtrate was acidified and the solution was extracted with EtOAc (3×20 mL). The combined organic layers were evaporated to dryness, the residue was treated with an aqueous solution of saturated NaHCO₃ (10 mL) and the insoluble material was separated by filtration. The filtrate was acidified with concentrated HCl and the cloudy solution extracted again with EtOAc (3×5 mL). The combined organic layers were concentrated to ~1 mL, causing crystallization of the product, which was collected by filtration to give pure (2-bromo-5-methoxy-4-sulfamoylphenyl)acetic acid (20 mg) 12f (~3% yield).

Synthesis of Inhibitors

Example 13

2-(2-Bromo-5-methoxy-4-sulfamoylphenyl)-N-[1-(4-methoxy-phenyl)-1-(2-methyl-6-piperidin-1-ylphenyl)methyl]acetamide (301)

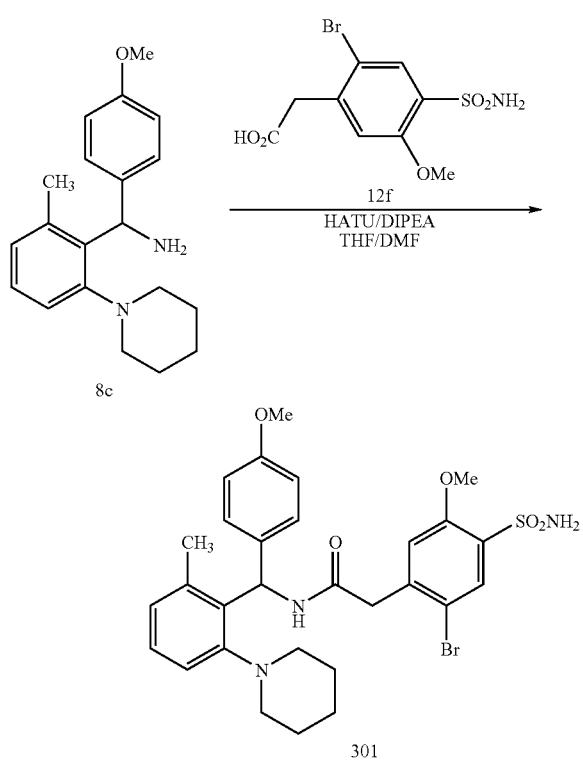

A reaction mixture containing (2-bromo-5-methoxy-4-sulfamoylphenyl)acetic acid 12f from Example 12 (18 mg, 0.06 mmol), 1-(4-methoxyphenyl)-1-(2-methyl-6-piperidin-1-ylphenyl)methylamine 8c from Example 8 (25.9 mg, 0.08 mmol), HATU (45.6 mg, 0.12 mmol) and DIPEA (0.06 ml, 0.3 mmol) in a solvent mixture of THF (1 mL) and DMF (0.3 mL) was stirred under argon at RT for 1 hour. The mixture was then diluted with EtOAc (7 mL) and the organic layer was washed with 1.0 M aqueous HCl (2 mL), saturated NaHCO₃ (2 mL), dried over Na₂SO₄, concentrated to a minimum volume (~1 mL) and purified by preparative TLC (eluent EtOAc:hexane:AcOH 60:40:1) to obtain 31 mg of the semi-pure final inhibitor (~85% purity by ¹H-NMR). The pure inhibitor 2-(2-bromo-5-methoxy-4-sulfamoylphenyl)-N-[1-(4-methoxyphenyl)-1-(2-methyl-6-piperidin-1-ylphenyl)methyl]acetamide 301 (Table 3) was isolated after further purification by C₁₈ reversed phase HPLC.

¹H NMR (400 MHz, DMSO, 325 K) δ: 1.2-1.6 (m, 4H, piperidine ring), 2.20 (s, 3H, —CH3), 2.5-2.8 m (2H, piperidine ring), 3.71 (s, 3H, —OCH₃), 3.85 (s, 3H, —OCH₃), 3.8-4.0 (m, 2H, —CO—CH₂—), 6.83 (d, J=8.3 Hz, 2H), 6.97 (br d, J=8.3 Hz, 2H), 7.1-7.2 (m, 4H), 7.30 (s, 1H), 7.83 (s, 1H), 8.36 (br s, NH).

ES⁺ MS m/z: 616.2 and 618.2 (M+H)⁺.

Example 14

5-Chloro-2-methoxy-4-{3-[(2-methyl-6-piperidin-1-yl-phenyl)(phenyl)methyl]ureido}benzoic acid (201)

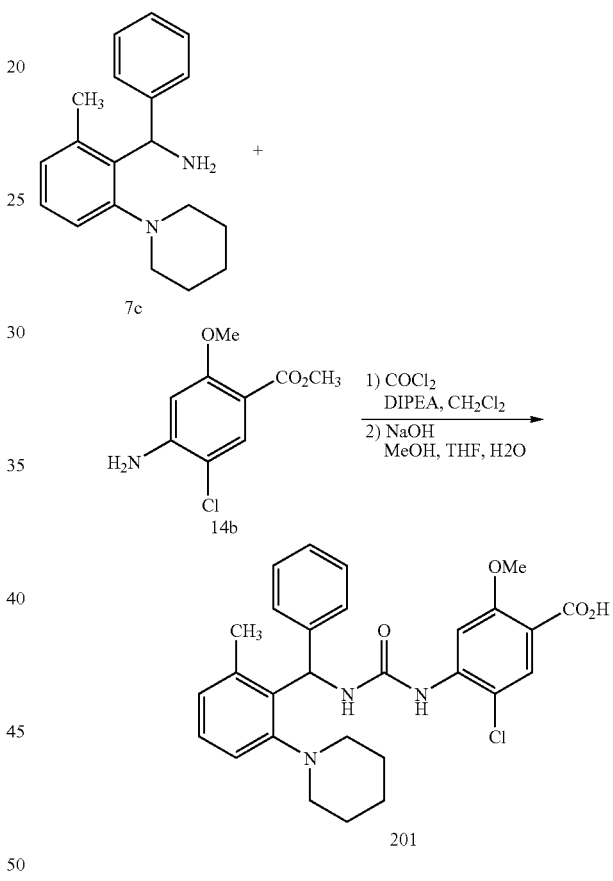

Methyl 4-amino-5-chloro-2-methoxybenzoate 14b (19.4 mg, 0.09 mmol), prepared from the commercially-available acid by standard esterification methods, was dissolved in dichloromethane (0.5 mL) and cooled to 0° C. for the successive addition of DIPEA (0.1 mL, 0.57 mmol) and phosgene (20% in toluene, 0.2 mL, 0.40 mmol). The reaction mixture was stirred for 2 h at RT and then concentrated under reduced pressure. The residue was dissolved in dichloromethane (0.5 mL) and then successively treated with DIPEA (0.1 mL, 0.57 mmol) and the intermediate amine 7c from Example 7 (25 mg, 0.089 mmol). The reaction mixture was stirred for 2 h at RT and then concentrated under vacuum. An aqueous solution of 5% KHSO₄ was added and the mixture was extracted with EtOAc. The organic layer was washed with brine and dried over anhydrous MgSO₄. After filtration and concentration the residue was dissolved in a mixture of THF (0.1 mL), methanol (0.2 mL) and water (0.2 mL) and then a 10 N aqueous NaOH solution (0.1 mL, 1.0 mmol) was added. The reaction mixture was stirred overnight at RT and then concentrated to dryness. The residue was dissolved in glacial acetic acid and purified by reversed phase HPLC to afford the desired compound 5-chloro-2-methoxy-4-{3-[(2-methyl-6-piperidin-1-ylphenyl)(phenyl)methyl]ureido}benzoic acid 201 (Table 2) as its TFA salt (23 mg, 48% yield).

$^1$H NMR (400 MHz, DMSO, 325 K) δ: 1.5-1.7 (m, 4H, piperidine ring), 2.02 (s, 3H, —CH$_3$), 2.8-2.9 m (2H, piperidine ring), 3.76 (s, 3H, —OCH$_3$), 6.94 (d, J=7.3 Hz, 1H), 7.08 (2d, J=7.6 Hz, 2H), 7.16-7.22 (m, 3H), 7.29 (dd, J=7.6 Hz, 1H), 7.7 (s, 1H), 7.70 (br, ~1H, NH), 8.16 (s, 1H), 8.64 (br, ~1H, NH).

ES$^+$ MS m/z: 509.3 (M+H)$^+$

Example 15

Determination of the Absolute Configuration of the HPV E1-E2 Interaction Inhibitor (105)

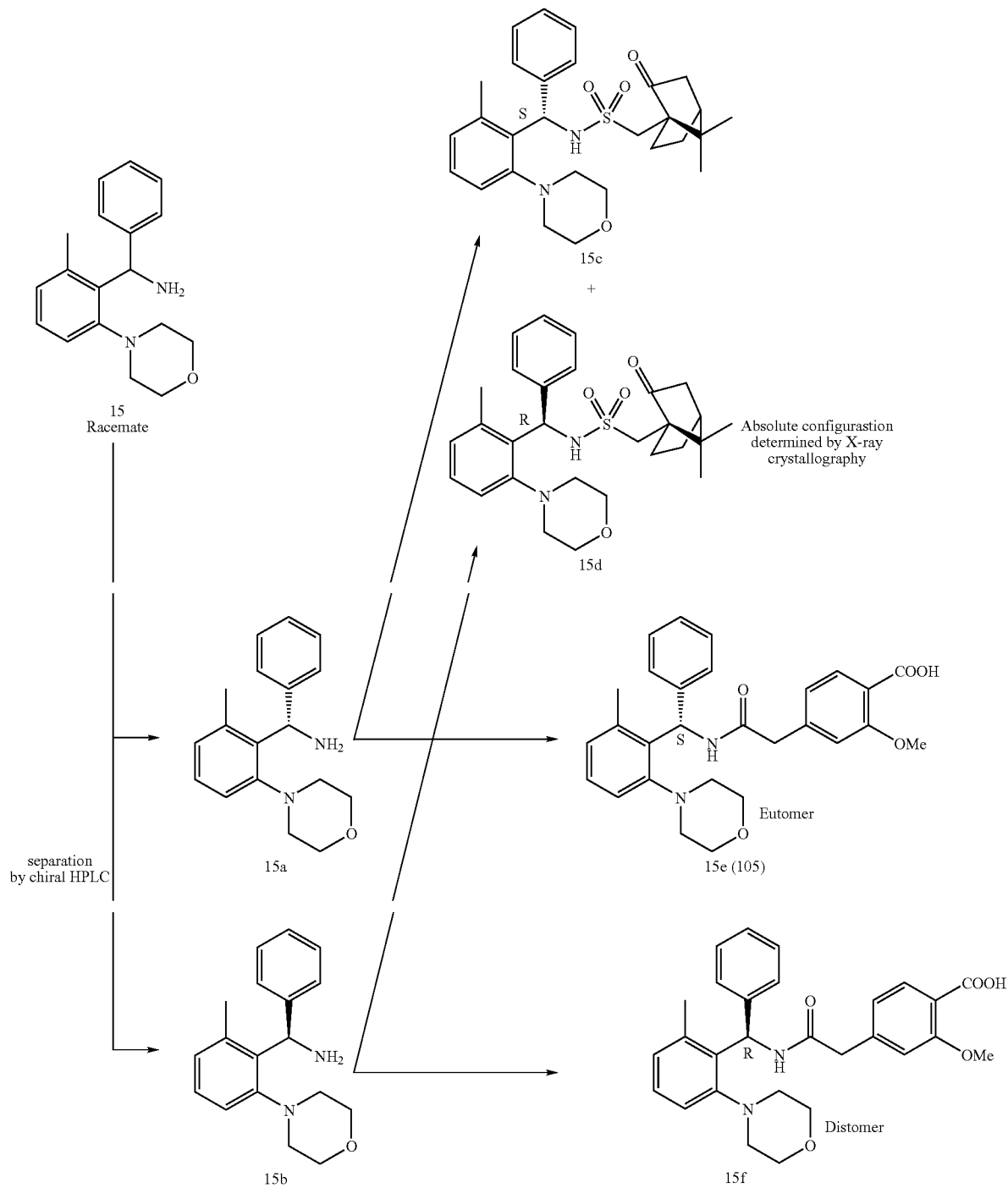

The racemic amine fragment precursor 15 (this amine fragment was prepared using methods analogous to those described in Examples 1 and 8) was separated into its two enantiomers 15a and 15b by chiral HPLC and the two enantiomerically enriched amines were coupled independently to camphor sulphonyl chloride to obtain compounds 15c and 15d; the latter compound produced high quality crystals for x-ray crystallography. For correlation purposes, the two enantiomerically-enriched samples (15a and 15b) were also coupled to a right-hand side carboxylic acid fragment to produce one potent inhibitor (the eutomer 15e) and the distomer (15f). X-ray crystallography of the sulfonamide 15d allowed assignment of this compound to the R-configuration at the previously unknown chiral center. The same amine precursor (15b) was also used to make the distomer 15f. In contrast the eutomer 15e (compound 105, Table 1) which was made from the S chiral amine 15a, was found to be a potent inhibitor in the HPV 11 E1-E2 DNA assay.

Example 16

E2-Dependent E1 DNA Binding Assay

The protocol for the E2-dependent E1 DNA binding assay is described in detail in WO 02/50082.

Example 17

SV40 T Antigen-DNA Binding Assay

The protocol for the SV40 T antigen DNA binding assay is described in detail in WO 02/50082.

Example 18

Cell-Based DNA Replication Assay

The protocol for the cell-based DNA replication assay is described in detail in WO 02/50082.

Example 19

Tables of Compounds

All compounds listed in Tables 1-4 were found to be active in the E1-E2 DNA assay referred to in Example 16 with an $IC_{50}$ value under 20 μM for HPV-11.

Certain compounds were also tested in the SV40 TAg assay of Example 17 and were found to be inactive or less active than in the E1-E2 DNA assay, providing good evidence that these compounds are selective against the papilloma virus.

In addition, at least one compound was tested in the DNA replication cellular assay of Example 18. The results obtained indicate that these compounds may be able to inhibit viral DNA replication.

TABLE 1

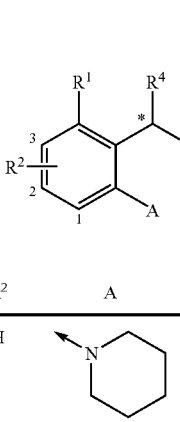

| Cpd | $R^1$ | $R^2$ | A | $R^{4*}$ | Y | $R^5$ | $R^6$ | MS $(M+H)^*$ |
|---|---|---|---|---|---|---|---|---|
| 101 | Me | H | 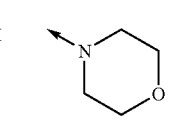 | Ph | $CH_2$ | OMe | H | 473.6 |
| 102 | Me | H | 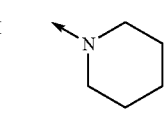 | Ph | $CH_2$ | OMe | H | 475.6 |
| 103 | Me | H | 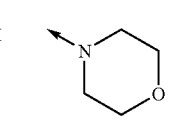 | Ph | NH | OMe | H | 474.6 |
| 104 | Me | H | 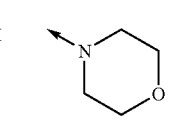 | 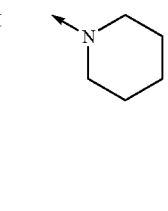 | $CH_2$ | OMe | H | 503.6 |

TABLE 1-continued

| Cpd | R¹ | R² | A | R⁴* | Y | R⁵ | R⁶ | MS (M+H)* |
|---|---|---|---|---|---|---|---|---|
| 105 | Me | H | morpholine (N-linked) | Ph (enantiomerically enriched) | $CH_2$ | OMe | H | 475.6 |
| 106 | Me | H | piperidine (N-linked) | —$(CH_2)_3$—$CH_3$ | $CH_2$ | OMe | Br | 531.3 |
| 107 | Me | H | piperidine (N-linked) | thiophen-3-yl | $CH_2$ | OMe | Br | 557.2 |
| 108 | Me | H | piperidine (N-linked) | thiophen-2-yl | $CH_2$ | OMe | Br | 557.2 |
| 109 | Me | H | piperidine (N-linked) | furan-2-yl | $CH_2$ | OMe | Br | 542.5 |
| 110 | H | 1-F | piperidine (N-linked) | 4-methoxyphenyl | $CH_2$ | OMe | Br | 585.2 |
| 111 | H | H | piperidine (N-linked) | 4-methoxyphenyl | $CH_2$ | OMe | Br | 569.2 |
| 112 | Me | H | piperidine (N-linked) | cyclohexyl | $CH_2$ | OMe | Br | 559.2 |

TABLE 1-continued
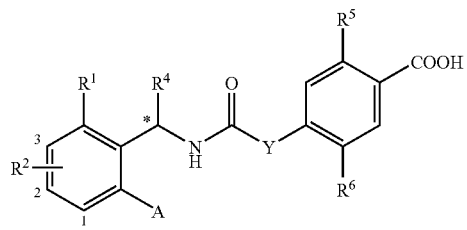
| Cpd | R¹ | R² | A | R⁴* | Y | R⁵ | R⁶ | MS (M+H)* |
|---|---|---|---|---|---|---|---|---|
| 113 | Et | H | piperidin-1-yl | 4-methoxyphenyl | $CH_2$ | OMe | Br | 597.1 |
| 114 | Me | H | piperidin-1-yl | Me | $CH_2$ | OMe | Br | 491.2 |
| 115 | Me | H | piperidin-1-yl | iPr | $CH_2$ | OMe | Br | 519.2 |
| 116 | Me | H | cyclohexyl | 4-methoxyphenyl | $CH_2$ | OMe | Br | 581.5 |
| 117 | Me | H | phenyl | 4-methoxyphenyl | $CH_2$ | OMe | Br | 575.4 |
| 118 | Me | H | cyclohexylamino | 4-methoxyphenyl | $CH_2$ | OMe | Br | 597.2 |
| 119 | Me | H | N-methyl-cyclohexylamino | 4-methoxyphenyl | $CH_2$ | OMe | Br | 611.2 |

TABLE 1-continued

| Cpd | R¹ | R² | A | R⁴* | Y | R⁵ | R⁶ | MS (M+H)* |
|---|---|---|---|---|---|---|---|---|
| 120 | Me | H | piperidine | benzo[1,3]dioxole | $CH_2$ | OMe | Br | 597.2 |
| 121 | Me | H | piperidine | naphthyl | $CH_2$ | OMe | Br | 603.2 |
| 122 | Me | H | piperidine | methoxynaphthyl | $CH_2$ | OMe | Br | 633.2 |
| 123 | Me | H | piperidine | methylnaphthyl | $CH_2$ | OMe | Br | 617.3 |
| 124 | Me | H | 4-methylpiperidine | methoxyphenyl | $CH_2$ | OMe | Br | 597.2 |
| 125 | Me | H | 4-phenoxypiperidine | methoxyphenyl | $CH_2$ | OMe | Br | 675.1 |

TABLE 1-continued

[Structure: substituted benzene with R¹, R², position numbers 1,2,3, A group, connected via CH(R⁴)(*)-NH-C(=O)-Y- to benzene with R⁵, R⁶, and COOH]

| Cpd | R¹ | R² | A | R⁴* | Y | R⁵ | R⁶ | MS (M+H)* |
|---|---|---|---|---|---|---|---|---|
| 126 | Me | H | 4,4-difluoropiperidin-1-yl | 4-methoxyphenyl (enantiomerically enriched) | CH₂ | OMe | Br | 619.1 |
| 127 | 3-thienyl | H | piperidin-1-yl | Me | CH₂ | OMe | Br | 559.2 |
| 128 | Me | H | piperidin-1-yl | 3-chlorophenyl | CH₂ | OEt | H | 522.1 |
| 129 | Me | H | piperidin-1-yl | Ph (enantiomerically enriched) | CH₂ | OEt | H | 487.6 |

*All compounds are racemic unless otherwise indicated.

TABLE 2

[Structure: substituted benzene with R⁴⁰, R⁴¹, R⁴², R⁴³, R⁴⁴, connected via CH(*)-NH-C(=O)-Y- to benzene with OMe, R⁵, and COOH; second phenyl with piperidine]

| Cpd | * | R⁴⁰ | R⁴¹ | R⁴² | R⁴³ | R⁴⁴ | Y | R⁶ | MS (M+H)* |
|---|---|---|---|---|---|---|---|---|---|
| 201 | — | H | H | H | H | H | NH | Cl | 509.3 |
| 202 | — | H | H | H | H | H | NH | Br | 553.5 |

TABLE 2-continued
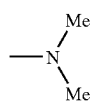
| Cpd | * | R40 | R41 | R42 | R43 | R44 | Y | R6 | MS (M+H)* |
|---|---|---|---|---|---|---|---|---|---|
| 203 | enantiomerically enriched | H | H | OMe | H | H | CH2 | Br | 581.2 |
| 204 | — | H | H | H | H | OMe | CH2 | Br | 581.2 |
| 205 | — | H | H | H | H | Me | CH2 | Br | 565.2 |
| 206 | — | H | H | Me | H | Me | CH2 | Br | 579.2 |
| 207 | — | H | H | H | OMe | H | CH2 | Br | 581.2 |
| 208 | — | H | H | H | —CH3 | H | CH2 | Br | 565.2 |
| 209 | — | H | H | —N(Me)Me | H | H | CH2 | Br | 594.3 |
| 210 | — | H | H | SMe | H | H | CH2 | Br | 597.2 |
| 211 | — | H | H | t-Bu | H | H | CH2 | Br | 607.3 |
| 212 | — | H | H | CF3 | H | H | CH2 | Br | 619.2 |
| 213 | — | H | H | Cl | H | H | CH2 | Br | 585.2 |
| 214 | — | H | H | 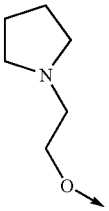 | H | H | CH2 | Br | 664.3 |
| 215 | — | H | H | OMe | H | OMe | CH2 | Br | 611.3 |
| 216 | — | OMe | H | OMe | H | OMe | CH2 | Br | 641.3 |
| 217 | — | H | H | H | H | iPr | CH2 | Br | 593.3 |
| 218 | — | H | Me | OMe | H | H | CH2 | Br | 541.2 |
| 219 | — | H | H | H | H | H | CH2 | Br | 552.2 |
| 220 | — | H | H | Ph | H | H | CH2 | Br | 647.2 |
*All compounds are racemic unless otherwise indicated.

TABLE 3

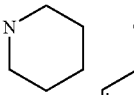

All compounds are racemic unless otherwise indicated.

| Cpd | $R^1$ | A | $R^4$ | Y | $R^5$ | $CR^6$—$X_2$ | $R^c$ | MS (M+H)* |
|---|---|---|---|---|---|---|---|---|
| 301 | Me | 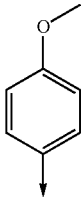 | 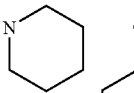 | $CH_2$ | OMe | CBr—CH | $SO_2NH_2$ | 618.2 |
| 302 | Me | 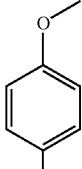 |  | $CH_2$ | H | | COOH | 523.3 |

TABLE 4

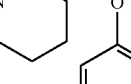
(VI)

All compounds are racemic unless otherwise indicated.

| Cpd | $R^1$ | A | $R^4$ | Y | Z | $X_3$ | $R^c$ | MS M(+H)* |
|---|---|---|---|---|---|---|---|---|
| 401 | Me | 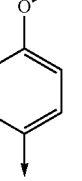 | 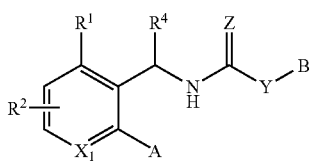 | NH | S | S | COOH | 496.2 |

What is claimed is:

1. A compound of formula (I) or its enantiomers or diastereoisomers thereof:

(I)

wherein $R^1$ is H, $(C_{1-6})$ alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl) amino, $(C_{3-7})$cycloalkyl, or phenyl;

$X_1$ is $CR^2$;

one or both free positions on the phenyl ring may be substituted with $R^2$ and each $R^2$ is independently: H, $(C_{1-6})$ alkyl, halo, $(C_{1-6})$haloalkyl, $(C_{1-6})$alkoxy, $(C_{1-6})$alkylthio, amino, $(C_{1-6})$alkylamino or di$((C_{1-6})$allyl)amino;

A is piperidinyl optionally substituted with one or more of $(C_{1-6})$alkyl, halo, $(C_{1-6})$haloalkyl, $(C_{1-6})$alkoxy, $(C_{1-6})$ alkylthio, amino, $(C_{1-6})$alkylamino, or di$((C_{1-6})$alkyl) amino, aryl, O-aryl, S-aryl, NH-aryl or $(C_{1-6})$alkyl-aryl;

$R^4$ is phenyl optionally substituted with one or more of $(C_{1-6})$alkyl, halo, $(C_{1-6})$haloalkyl, $(C_{1-6})$alkylthio, amino, $(C_{1-6})$alkylamino, di$((C_{1-6})$alkyl)amino, aryl, $(C_{1-6})$alkyl-aryl, or $(C_{1-6})$alkoxy, wherein said $(C_{1-6})$ alkoxy is optionally substituted with aryl;

Z is O or S;

Y is $CH_2$ or NH;

B is:

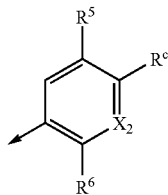

wherein $R^5$ is $(C_{3-7})$cycloalkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl;

$X_2$ is $CR^7$;

$R_6$ is halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl; and $R^7$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl; and $R^C$ is COOH, CONHR$^9$, SO$_2$NHR$^9$, CONHSO$_2$R$^9$ or CONHSO$_2$NHR$^9$, wherein R$^9$ is H, $(C_{1-6})$alkyl, $(C_{3-6})$cycloalkyl or phenyl; provided that when Y is NH, R$^6$ cannot be hydroxyl or sulfhydryl;

or a pharmaceutically-acceptable salt or ester thereof.

2. The compound according to claim 1 wherein $R^1$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, $(C_{3-7})$cycloalkyl, or phenyl;

$X_1$ is $CR^2$;

each $R^2$ is independently H, $(C_{1-6})$alkyl, halo, $(C_{1-6})$haloalkyl, $(C_{1-6})$alkoxy, $(C_{1-6})$alkylthio, amino, $(C_{1-6})$alkylamino or di$((C_{1-6})$alkyl)amino;

A is piperidinyl optionally substituted with:
$(C_{1-6})$alkyl, halo, $(C_{1-6})$haloalkyl, $(C_{1-6})$alkoxy, $(C_{1-6})$alkylthio, amino, $(C_{1-6})$alkylamino, or di$((C_{1-6})$alkyl)amino, aryl, O-aryl, S-aryl, NH-aryl or $(C_{1-6})$alkyl-aryl;

$R^4$ is phenyl optionally substituted with:
$(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, aryl, $(C_{1-6})$alkyl-aryl or $(C_{1-6})$alkoxy-aryl;

Z is O or S;

Y is CH$_2$, or NH;

B is:

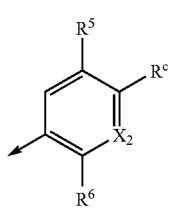

wherein $R^5$ is $(C_{3-7})$cycloalkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl;

$X_2$ is $CR^7$;

$R^6$ is halo, $(C_{1-6})$haloalkyl, $(C_{1-6})$alkoxy, $(C_{1-6})$alkylthio, amino, $(C_{1-6})$aklkylamino, di$((C_{1-6})$alkyl)amino, hydroxyl or sulfhydryl; and $R^7$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino, hydroxyl or sulfhydryl;

$R^C$ is COOH, CONHR$^9$ or SO$_2$NHR$^9$, wherein R$^9$ is H, $(C_{1-6})$alkyl, $(C_{3-6})$cycloalkyl or phenyl; provided that when Y is NH, R$^6$ cannot be hydroxyl or sulfhydryl;

or a pharmaceutically-acceptable salt or ester thereof.

3. The compound according to claim 1 wherein $R^1$ is methyl or ethyl.

4. The compound according to claim 1 wherein A is 1-piperidinyl optionally mono- or di- substituted with: $(C_{1-6})$alkyl, halo, $(C_{1-6})$haloalkyl or phenoxy.

5. The compound according to claim 4 wherein A is 1-piperidinyl optionally mono- or di-substituted with halo or phenoxy, and $R^1$ is H or $(C_{1-6})$alkyl.

6. The compound according to claim 1 wherein $R^4$ is phenyl, optionally independently substituted with one to four of methoxy, halo, or phenyl.

7. The compound according to claim 1 wherein $R_5$ is methoxy or ethoxy.

8. The compound according to claim 1 wherein $R^6$ is halo.

9. The compound according to claim 1 wherein $R^1$ is H, $(C_{1-6})$alkyl, halo, $(C_{1-6})$haloalkyl, $(C_{1-6})$alkoxy, $(C_{1-6})$alkylthio, amino, $(C_{1-6})$alkylamino, or di$((C_{1-6})$alkyl)amino;

$X_1$ is $CR^2$;

each $R^2$ independently H or halo;

A is piperidinyl optionally independently substituted with one or more of
$(C_{1-6})$alkyl, halo, $(C_{1-6})$haloalkyl, $(C_{1-6})$alkoxy, $(C_{1-6})$alkylthio, amino, $(C_{1-6})$alkylamino, di$((C_{1-6})$alkyl)amino or aryloxy;

$R^4$ phenyl optionally independently substituted with one or more of $(C_{1-6})$alkyl, halo, $(C_{1-6})$haloalkyl, $(C_{1-6})$alkylthio, amino, $(C_{1-6})$alkylamino, di$((C_{1-6})$alkyl)amino, aryl, $(C_{1-6})$alkyl-aryl, or $(C_{1-6})$alkoxy, wherein said $(C_{1-6})$alkoxy is optionally substituted with aryl;

Z is O;

Y is CH$_2$ or NH;

B is:

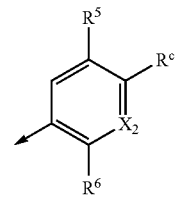

wherein $R^5$ is halo, $(C_{1-6})$haloalkyl, $(C_{1-6})$alkoxy, $(C_{1-6})$alkylthio, $(C_{1-6})$alkylamino, or di$((C_{1-6})$alkyl)amino;

$X_2$ is $CR^7$;

$R^6$ is halo, $(C_{1-6})$haloalkyl, $(C_{1-6})$alkoxy, $(C_{1-6})$alkylthio, $(C_{1-6})$alkylamino, or di$((C_{1-6})$alkyl)amino and $R^7$ is H, $(C_{1-6})$alkyl, halo, $(C_{1-6})$haloalkyl, $(C_{1-6})$alkoxy, $(C_{1-6})$alkylthio, $(C_{1-6})$alkylamino, or di$((C_{1-6})$alkyl)amino, and $R^C$ is COOH, or SO$_2$NH$_2$.

10. The compound according to claim 1 wherein $R^1$ is $(C_{1-6})$alkyl;

$X_1$ is CH;

$R^2$ is H;

A is piperidinyl optionally independently substituted with one or more of $(C_{1-6})$alkyl, halo, $(C_{1-6})$haloalkyl or aryloxy;

$R^4$ phenyl optionally independently substituted with one or more of $(C_{1-6})$alkyl, halo, $(C_{1-6})$haloalkyl, $(C_{1-6})$alkylthio, amino, $(C_{1-6})$alkylamino, di($(C_{1-6})$alkyl)amino, aryl, and $(C_{1-6})$alkoxy, wherein said $(C_{1-6})$alkoxy is optionally substituted with aryl;

Z is O;
Y is $CH_2$;
B is:

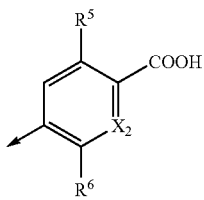

wherein $R^5$ is $(C_{1-6})$alkoxy;
$X_2$ is $CR^7$;
$R^6$ is halo or $(C_{1-6})$haloalkyl, and $R^7$ is H.

11. The compound according to claim 1 wherein
$R^1$ is H, methyl, or ethyl;
both $X_1$ and $X_2$ are CH;
each $R^2$ is independently H or halo;
A is 1-piperidyl, said 1-piperidyl being optionally mono- or di- substituted with:
$(C_{1-6})$alkyl, halo, $(C_{1-6})$haloalkyl, or aryloxy;
$R^4$ phenyl optionally independently substituted with one or more of $(C_{1-6})$alkyl, halo, $(C_{1-6})$haloalkyl, $(C_{1-6})$alkylthio, amino, $(C_{1-6})$alkylamino, di($(C_{1-6})$alkyl)amino, aryl, or $(C_{1-6})$alkoxy, wherein said $(C_{1-6})$alkoxy is optionally substituted with aryl;
Z is O;
Y is $CH_2$ or NH;
B is:

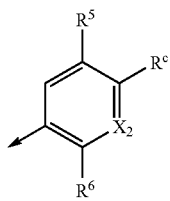

$R^5$ is methoxy or ethoxy;
$R^6$ is halo; and
$R^C$ is COOH.

12. The compound according to claim 1 wherein
$R^1$ is H or methyl;
$X_1$ is CH;
$R^2$ is H;
A is 1-piperidinyl, said 1-piperidinyl being optionally substituted with Me or phenoxy or optionally geminally difluorinated;
$R^4$ naplithyl optionally substituted with: methoxy or $(C_{1-6})$alkyl, or $R^4$ is phenyl optionally substituted with one to four of: methoxy, halo, or phenyl;
Z is O;
Y is $CH_2$;

B is:

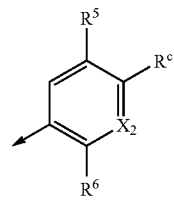

$R^5$ is methoxy;
$X_2$ is CH;
$R^6$ is bromo; and
$R^C$ is COOH.

13. The compound according to claim 1, or its enantiomers or diastereomers thereof, of the formula

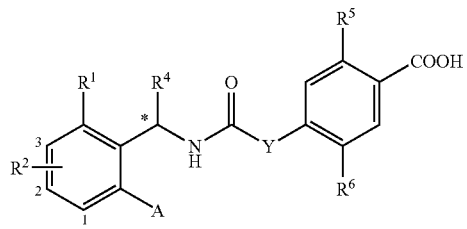

wherein $R^1$, $R^2$, A, $R^4$, Y, $R^5$ and $R^6$ are defined as in the table below; wherein with respect to $R^2$, the number indicates the position of substitution on the phenyl ring:

| Cpd | $R^1$ | $R^2$ | A | $R^4$ | Y | $R^5$ | $R^6$ |
|---|---|---|---|---|---|---|---|
| 110 | H | 1-F | piperidinyl | phenoxyphenyl | $CH_2$ | OMe | Br |
| 111 | H | H | piperidinyl | phenoxyphenyl | $CH_2$ | OMe | Br |
| 113 | Et | H | piperidinyl | phenoxyphenyl | $CH_2$ | OMe | Br |

-continued

| Cpd | R¹ | R² | A | R⁴ | Y | R⁵ | R⁶ |
|---|---|---|---|---|---|---|---|
| 124 | Me | H | 4-methylpiperidinyl | 4-OMe-phenyl | CH₂ | OMe | Br |
| 125 | Me | H | 4-phenoxypiperidinyl | 4-OMe-phenyl | CH₂ | OMe | Br |
| 126 | Me | H | 4,4-difluoropiperidinyl | 4-OMe-phenyl | CH₂ | OMe | Br |

14. The compound according to claim 1, or its enantiomers or diastereomers thereof, of the formula

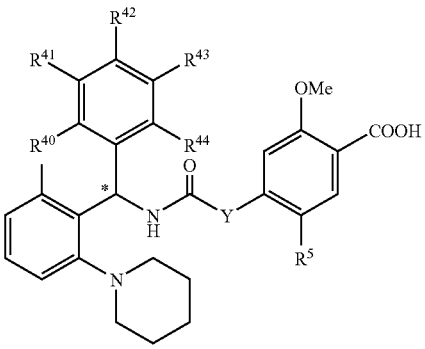

wherein R⁴⁰, R⁴¹, R⁴², R⁴³, R⁴⁴, Y, and R⁶ are defined as in the table below:

| Cpd | R⁴⁰ | R⁴¹ | R⁴² | R⁴³ | R⁴⁴ | Y | R⁶ |
|---|---|---|---|---|---|---|---|
| 201 | H | H | H | H | H | NH | Cl |
| 202 | H | H | H | H | H | NH | Br |
| 203 | H | H | OMe | H | H | CH₂ | Br |
| 204 | H | H | H | H | OMe | CH₂ | Br |
| 205 | H | H | H | H | Me | CH₂ | Br |
| 206 | H | H | Me | H | Me | CH₂ | Br |
| 207 | H | H | H | OMe | H | CH₂ | Br |
| 208 | H | H | H | —CH₃ | H | CH₂ | Br |

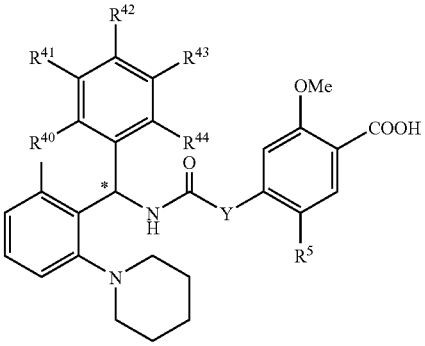

wherein R⁴⁰, R⁴¹, R⁴², R⁴³, R⁴⁴, Y, and R⁶ are defined as in the table below:

| Cpd | R⁴⁰ | R⁴¹ | R⁴² | R⁴³ | R⁴⁴ | Y | R⁶ |
|---|---|---|---|---|---|---|---|
| 209 | H | H | N(Me)₂ | H | H | CH₂ | Br |
| 210 | H | H | SMe | H | H | CH₂ | Br |
| 211 | H | H | t-Bu | H | H | CH₂ | Br |
| 212 | H | H | CF₃ | H | H | CH₂ | Br |
| 213 | H | H | Cl | H | H | CH₂ | Br |
| 215 | H | H | OMe | H | OMe | CH₂ | Br |
| 216 | OMe | H | OMe | H | OMe | CH₂ | Br |
| 217 | H | H | H | H | iPr | CH₂ | Br |
| 218 | H | Me | OMe | H | H | CH₂ | Br |
| 219 | H | H | H | H | H | CH₂ | Br |
| 220 | H | F | Ph | H | H | CH₂ | Br |

15. The compound according to claim 1, or its enantiomers or diastereomers thereof, of the formula

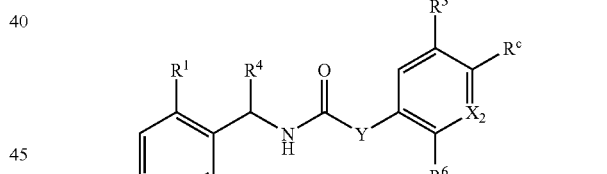

wherein R¹, A, R⁴, Y, R⁵, R⁶, X₂, and Rᶜ are defined as in the table below:

| Cpd | R¹ | A | R⁴ | Y | R⁵ | CR⁶=X₂ | Rᶜ |
|---|---|---|---|---|---|---|---|
| 301 | Me | piperidinyl | 4-OMe-phenyl | CH₂ | OMe | CBr=CH | SO₂NH₂ |

* * * * *